(12) United States Patent
Braun et al.

(10) Patent No.: US 8,333,783 B2
(45) Date of Patent: Dec. 18, 2012

(54) OCCLUSION DEVICE AND METHOD OF USE

(75) Inventors: Michael Braun, Backnang (DE); John S. Geis, Bad Zwischenahn (DE)

(73) Assignee: Reverse Medical Corporation, Irvine, CA (US)

( * ) Notice: Subject to any disclaimer, the term of this patent is extended or adjusted under 35 U.S.C. 154(b) by 615 days.

(21) Appl. No.: 12/024,974

(22) Filed: Feb. 1, 2008

(65) Prior Publication Data
US 2008/0200946 A1   Aug. 21, 2008

Related U.S. Application Data

(60) Provisional application No. 60/890,340, filed on Feb. 16, 2007.

(51) Int. Cl.
*A61M 29/00* (2006.01)

(52) U.S. Cl. ........................................................ 606/194

(58) Field of Classification Search .................. 606/159, 606/194, 198, 200; 604/96.01, 101.01–101.03, 604/101.05; 623/1.11, 1.12
See application file for complete search history.

(56) References Cited

U.S. PATENT DOCUMENTS

| | | | |
|---|---|---|---|
| 5,626,601 A * | 5/1997 | Gershony et al. | ............. 606/194 |
| 6,146,370 A | 11/2000 | Barbut | |
| 6,161,547 A | 12/2000 | Barbut | |
| 6,206,868 B1 | 3/2001 | Parodi | |
| 6,295,989 B1 | 10/2001 | Connors, III | |
| 6,413,235 B1 | 7/2002 | Parodi | |
| 6,423,032 B2 | 7/2002 | Parodi | |
| 6,511,497 B1 | 1/2003 | Braun | |
| 6,533,800 B1 | 3/2003 | Barbut | |
| 6,540,712 B1 | 4/2003 | Parodi et al. | |
| 6,558,356 B2 | 5/2003 | Barbut | |
| 6,562,058 B2 | 5/2003 | Seguin et al. | |
| 6,582,396 B1 | 6/2003 | Parodi | |
| 6,582,448 B1 * | 6/2003 | Boyle et al. | ................... 606/200 |

(Continued)

FOREIGN PATENT DOCUMENTS
EP   0321912 A1   6/1989

OTHER PUBLICATIONS
Kachel, R., Results of Balloon Angioplasty in the Carotid Arteries, J. Endovasc. Surg., 1996; 3:22-30.

(Continued)

*Primary Examiner* — Ryan Severson
*Assistant Examiner* — Katherine M Shi
(74) *Attorney, Agent, or Firm* — K. David Crockett, Esq.; Crockett & Crockett, PC

(57) ABSTRACT

A device for protecting cerebral vessels or brain tissue during treatment of a carotid vessel includes a catheter having a distal portion, a proximal portion and a lumen extending therebetween, the catheter including first and second expandable areas for vessel occlusion provided over the length of the catheter. The device further includes an elongate stretching member insertable longitudinally through the lumen of the catheter, the elongate stretching member being configured for stretching at least a portion of the catheter and causing the first and second expandable areas to transition from an expanded state to a collapsed state, and wherein the elongate stretching member is retracted proximally relative to the catheter causes the first and second expandable areas to transition from the collapsed state to a radially, or laterally expanded state.

10 Claims, 12 Drawing Sheets

U.S. PATENT DOCUMENTS

| Patent No. | Date | Name | Ref |
|---|---|---|---|
| 6,595,953 B1 * | 7/2003 | Coppi et al. | 604/96.01 |
| 6,595,980 B1 | 7/2003 | Barbut | |
| 6,605,074 B2 | 8/2003 | Zadno-Azizi et al. | |
| 6,623,471 B1 | 9/2003 | Barbut | |
| 6,626,886 B1 | 9/2003 | Barbut | |
| 6,632,236 B2 | 10/2003 | Hogendijk | |
| 6,641,573 B1 | 11/2003 | Parodi | |
| 6,796,992 B2 | 9/2004 | Barbut | |
| 6,830,579 B2 | 12/2004 | Barbut | |
| 6,837,881 B1 | 1/2005 | Barbut | |
| 6,840,949 B2 | 1/2005 | Barbut | |
| 6,848,448 B1 | 2/2005 | St. Germain et al. | |
| 6,858,019 B2 | 2/2005 | McGuckin, Jr. et al. | |
| 6,878,140 B2 | 4/2005 | Barbut | |
| 6,887,227 B1 | 5/2005 | Barbut | |
| 6,902,540 B2 * | 6/2005 | Dorros et al. | 604/8 |
| 6,905,490 B2 | 6/2005 | Parodi | |
| 6,908,474 B2 | 6/2005 | Hogendijk | |
| 6,929,634 B2 | 8/2005 | Dorros et al. | |
| 7,063,714 B2 | 6/2006 | Dorros et al. | |
| 7,083,594 B2 | 8/2006 | Coppi | |
| 7,150,736 B2 | 12/2006 | Barbut et al. | |
| 7,166,097 B2 | 1/2007 | Barbut | |
| 7,232,432 B2 | 6/2007 | Fulton, III et al. | |
| 7,235,095 B2 | 6/2007 | Haverkost et al. | |
| 2001/0041860 A1 | 11/2001 | Barbut | |
| 2001/0044598 A1 | 11/2001 | Parodi | |
| 2001/0047184 A1 | 11/2001 | Connors | |
| 2002/0087119 A1 | 7/2002 | Parodi | |
| 2002/0091349 A1 * | 7/2002 | Reich | 604/5.01 |
| 2002/0115982 A1 | 8/2002 | Barbut | |
| 2002/0161392 A1 | 10/2002 | Dubrul | |
| 2002/0165573 A1 | 11/2002 | Barbut | |
| 2002/0169458 A1 | 11/2002 | Connors | |
| 2003/0023200 A1 | 1/2003 | Barbut | |
| 2003/0023204 A1 * | 1/2003 | Vo et al. | 604/103.07 |
| 2003/0040694 A1 | 2/2003 | Dorros | |
| 2003/0040704 A1 | 2/2003 | Dorros | |
| 2003/0040705 A1 | 2/2003 | Dorros | |
| 2003/0040762 A1 | 2/2003 | Dorros | |
| 2003/0097036 A1 | 5/2003 | Germain | |
| 2003/0171769 A1 | 9/2003 | Barbut | |
| 2003/0173815 A1 | 9/2003 | De Maina | |
| 2003/0195382 A1 | 10/2003 | Barbut | |
| 2003/0199913 A1 | 10/2003 | Dubrul | |
| 2004/0098017 A1 | 5/2004 | Saab et al. | |
| 2004/0127885 A1 | 7/2004 | Barbut | |
| 2004/0176832 A1 * | 9/2004 | Hartley et al. | 623/1.11 |
| 2004/0260333 A1 | 12/2004 | Dubrul | |
| 2005/0085685 A1 | 4/2005 | Barbut | |
| 2005/0090854 A1 | 4/2005 | Barbut | |
| 2005/0124931 A1 | 6/2005 | Fulton | |
| 2005/0124973 A1 | 6/2005 | Dorros | |
| 2005/0131453 A1 | 6/2005 | Parodi | |
| 2005/0149103 A1 | 7/2005 | Connors | |
| 2005/0149112 A1 | 7/2005 | Barbut | |
| 2005/0159640 A1 | 7/2005 | Barbut | |
| 2005/0228432 A1 | 10/2005 | Hogendijk | |
| 2005/0267323 A1 | 12/2005 | Dorros | |
| 2005/0273051 A1 | 12/2005 | Coppi | |
| 2005/0277979 A1 | 12/2005 | Dorros et al. | |
| 2006/0100694 A1 * | 5/2006 | Globerman | 623/1.35 |
| 2007/0118095 A1 | 5/2007 | Barbut | |
| 2007/0135793 A1 | 6/2007 | Barbut | |
| 2007/0198049 A1 | 8/2007 | Barbut | |

OTHER PUBLICATIONS

Theron, J., Letters to the Editors, J. Endovasc. Surg., 1996; 3:484-486.
MO.MA, Proximal Flow Blockage Cerebral Protection Device. Product Brochure (undated).
GORE Neuro Protection System, Instructions for Use, Apr. 2006.
Henry et al., Carotid Angioplasty and Stenting 1998.
European Search Report dated Sep. 14, 2010 in related European Patent Application No. 08729319.7.

* cited by examiner

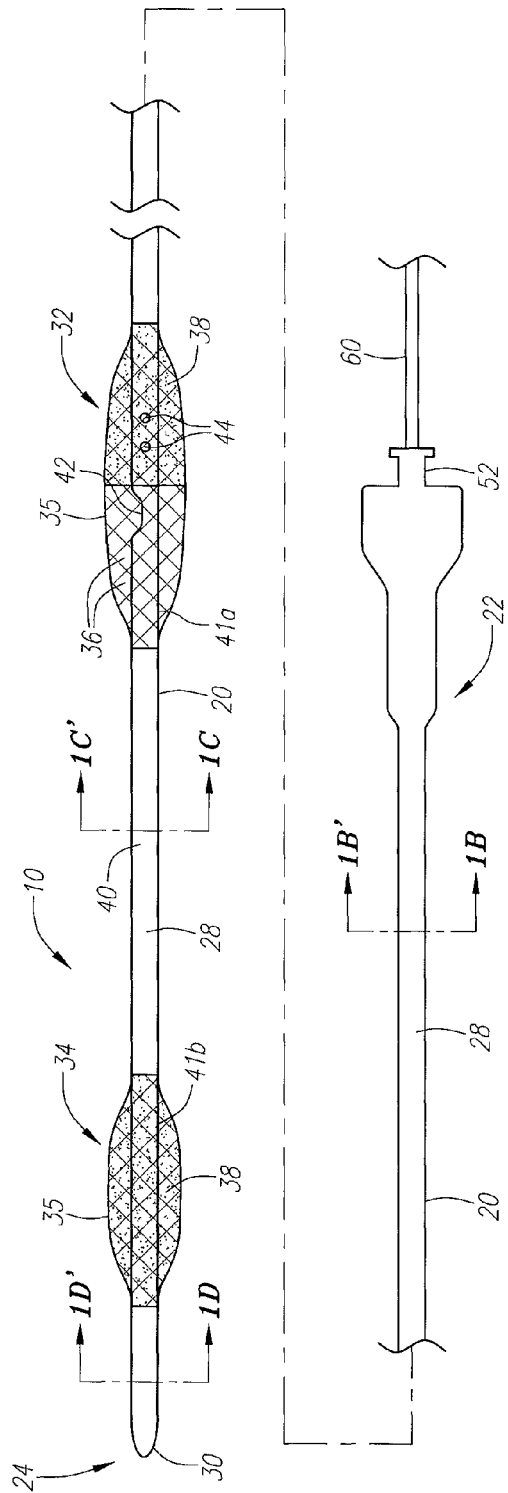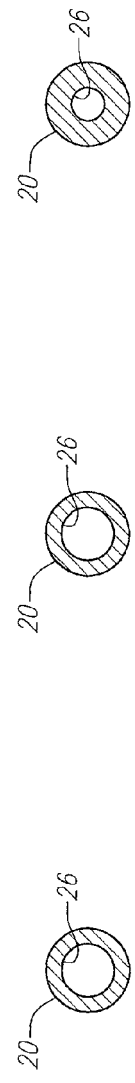
FIG. 1A
FIG. 1B
FIG. 1C
FIG. 1D

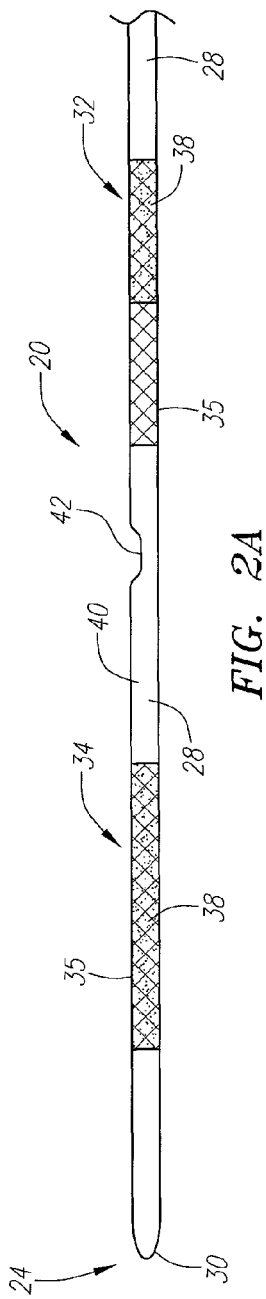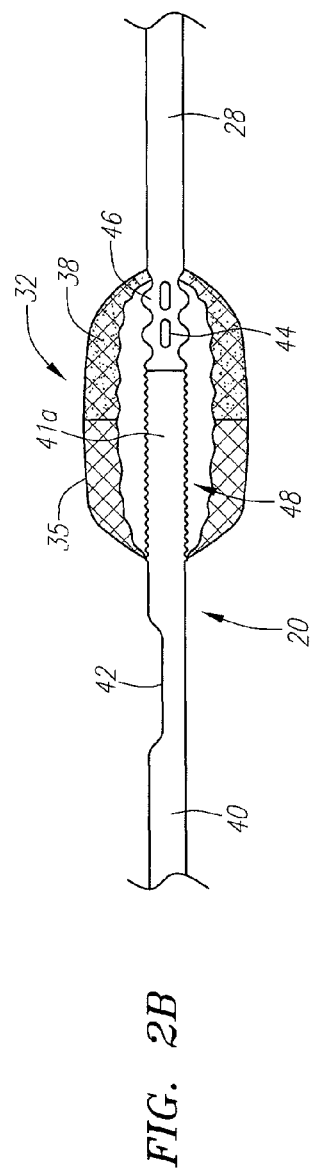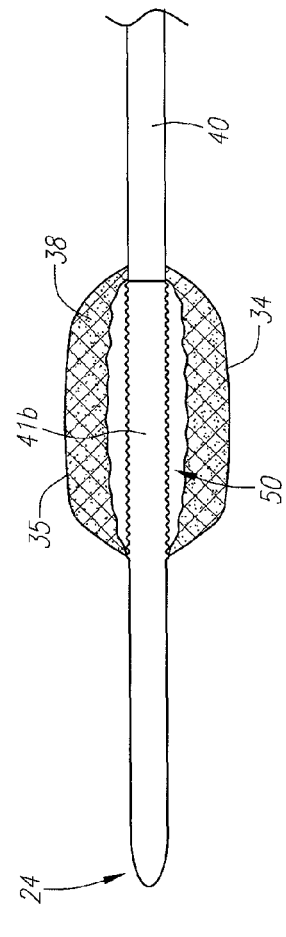
FIG. 2A
FIG. 2B
FIG. 2C

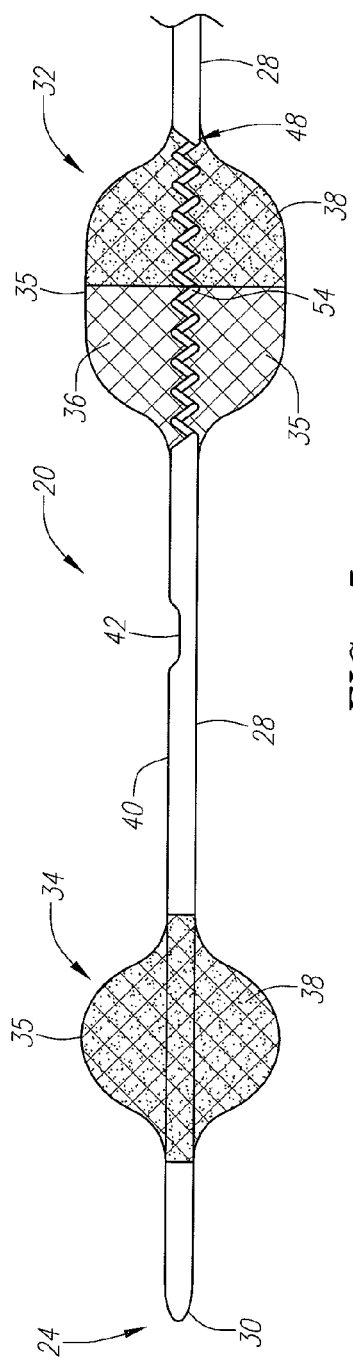
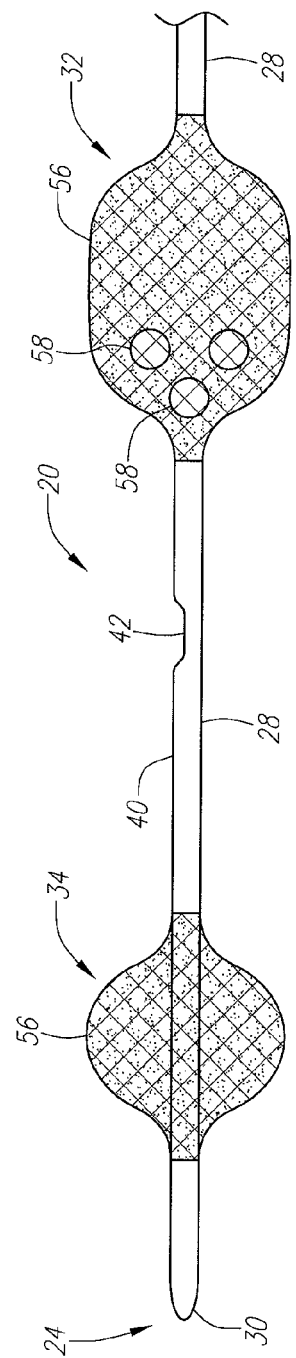
FIG. 5
FIG. 6

OCCLUSION DEVICE AND METHOD OF USE

REFERENCE TO RELATED APPLICATIONS

This Application claims priority to U.S. Provisional Patent Application No. 60/890,340 filed on Feb. 16, 2007 pursuant to 35 U.S.C. §119. U.S. Patent Application No. 60/890,340 is hereby incorporated by reference as if set forth fully herein.

FIELD OF THE INVENTION

The field of the invention generally relates to devices and methods for protecting cerebral vessels and brain tissue during treatment of the carotid vessels. More particularly, the field of the invention pertains to devices and methods for inducing retrograde flow within the carotid vessels so as to eliminate the migration of particulate matter in the direction of normal cerebral blood flow.

BACKGROUND OF THE INVENTION

In the case of stenosis in the carotid artery, atherosclerotic plaques are present at the vessel wall of the external carotid artery, the internal carotid artery, or the common carotid artery. These plaques have to be removed as they hinder the blood flow. A number of catheter-based angioplasty procedures as well as various surgical and non-surgical procedures have been developed for this reason. There is, however, a risk with these procedures, whereby parts of the plaque or other material may loosen and be released as emboli into the blood stream. In particular, such released particles can migrate in the direction toward the cerebral blood vessels due to the antegrade (i.e., forward moving) blood flow. The emboli have a high probability of becoming lodged within the cerebrovasculature causing flow blockage, brain tissue ischemia, and cell death. This represents a major risk for the patient. Vessel filters, which are supposed to block micro and macro-sized particles, have been developed in order to minimize or avoid these risks.

Conventional filter devices are disadvantageous in that they have to be positioned in a distal position relative to the stenosis in order to catch the released or sloughed off particles, which, according to the natural antegrade blood flow, would be transported towards the cerebral brain tissues and ultimately the brain. These vessel filters thus have to be guided beyond the stenosis before they can be deployed. Unfortunately, the process of guiding the filter through the area of the stenosis may itself result in the dislodging of particulate matter, which then may lead to emboli.

A so-called proximal protection system has been suggested as an additional protection against such risks. This system uses the selective placement of two inflatable balloons to effect retrograde blood flow (i.e., a reversal of the blood flow direction). For example, the MO.MA cerebral protection device developed by Invatec (Italy) operates on this principal. In the MO.MA system a catheter device includes two inflatable balloons, which serve to occlude the suitable vessels and generate a reverse blood flow. In this design, the main catheter is essentially a balloon catheter having two inflation lumens that communicate with the two inflatable balloons. A working lumen is provided in the catheter where an external instrument can be guided to treat the stenosis.

Another system developed by W. L. Gore & Associates, Inc. (GORE Neuro Protection System) utilizes a catheter having an inner lumen along with a distally located inflatable balloon sheath. A separate balloon wire is guided within the inner lumen of the catheter. The balloon wire is advanced into the external carotid artery (if the stenosis is present in the internal carotid artery) and the balloon is expanded to occlude the external carotid artery. Antegrade blood flow in the direction of the external carotid artery will thereby be stopped. The second inflatable balloon sheath, which is positioned at the distal end of the balloon catheter, is then inflated to occlude the common carotid artery. The blood flow of the common carotid artery will thus be stopped. Flow reversal is achieved at the treatment site by selective occlusion of the external carotid artery and the common carotid artery. Blood that tries to flow from the internal carotid artery to the common carotid artery will be hindered by the balloon sheath of the balloon catheter and instead is guided into the lumen of the balloon catheter for filtration and subsequent redirection into the patient via venous return. A working device such as a dilation balloon catheter, which is necessary for the further dilation of the stenosis, is guided within the balloon catheter lumen.

By inducing retrograde blood flow, the above-mentioned systems can potentially avoid a migration of particles in the direction of the cerebral blood vessels. Also, a penetration of the area of the stenosis is not necessary. The above-noted systems are, however, disadvantageous because they require relatively large dimensions. In particular, the inner diameter of the balloon catheter has to be large due to the various system components to be guided therein (e.g., external balloon and other intervention tools). In addition, the incorporation of the inflation lumen(s) into the catheter makes for devices having larger diameters and reduced space available for the working lumen. This is a particular concern because the sizes of the therapeutic and diagnostic tools for carotid artery intervention are constrained due to the limited space available within the balloon catheter. It may not be possible to adapt the size of the intervention tools to the required small size.

There thus is a need for improved methods and devices for occluding one or more vessels to protect cerebral vessels and the brain. For instance, there is a need to have occlusion devices that have a relatively low profile (e.g., outer diameter). Smaller devices are more manageable to handle at the vascular access site (e.g., femoral artery) and offer additional flexibility through the tortuous vascular anatomy. There is a need for an occlusion device that is easier to use than the devices described above. For example, the GORE Neuro Protection System uses separate elongate devices having inflatable balloons thereon. A single device that incorporates both proximal and distal occlusive elements is easier to use. In addition, an occlusion device should be able to be used with a single guidewire that can be used for protection device deployment as well as delivery of a working instrument such as a stent or balloon catheter.

Additionally, there is a need for a device that incorporates a single step to deploy the proximal and distal occlusion elements. For example, in the MO.MA cerebral protection device, two separate inflation lumens (one for proximal balloon and one for distal balloon) must be actuated for full deployment of the occlusive balloons. For full deployment of the balloons in the GORE Neuro Protection device, as explained above, the user must inflate the balloon wire in addition to the separate balloon sheath located on the distal end of the catheter. In addition, it would be preferably to provide a device having occlusive elements that do not need the cumbersome and space-occupying inflation lumens used in balloon-based devices. The device should also have the ability to rapidly re-establish normal or antegrade flow given the potential for occlusion intolerance in the patient. Finally, the device should offer near constant procedural imaging capability.

SUMMARY OF THE INVENTION

In a first aspect of the invention, a device for protecting cerebral vessels or brain tissue during treatment of carotid vessels includes a catheter having a distal portion, a proximal portion, and lumen extending therebetween. The catheter includes first and second expandable areas for vessel occlusion that are provided over a length of the catheter. In another embodiment, the catheter can comprise more than two expandable areas. The device includes a removable elongate stretching member that is insertable longitudinally through the lumen of the catheter. The elongate stretching member is configured for stretching at least a portion of the catheter and causing the first and second expandable areas to transition from an expanded state to a collapsed state. When the elongate member is retracted proximally relatively to the catheter, the first and second expandable areas transition from the collapsed state to an expanded state. In one aspect of the invention, the expandable areas expand at substantially the same time. The collapsed state refers to a state wherein the expandable area comprises a first, smaller diameter, radius, or cross-sectional configuration. The expanded state refers to a state wherein the expandable area comprises a second, larger diameter, radius, or cross-sectional configuration.

The expandable areas can be formed from self-expandable members disposed along the length of the catheter or they can be areas of the catheter body itself that are forced by a separate component of the expandable area to expand. Expandable areas are regions of the catheter, which assume the expanded state due to changes of external influences and maintain the expanded state without further influence from the outside. The expansion generally occurs in the radial direction of the longitudinal axis of the catheter. The change of external influences can, for example, be the removal of a mechanical or magnetic force being imposed onto the area or a change in temperature. The lateral cross-sectional configuration of the expandable areas in the expanded state can comprise shapes including but not limited to spherical, elliptical, oblong, or cylindrical. In the collapsed or stretched state, the expandable areas can assume the shape of a cylinder or tube and preferably have an outer diameter corresponding substantially to the outer diameter of the catheter tube or body on/in which these areas are provided.

The device allows for the occlusion of two vessels, and in particular, vessels having a bifurcation area from which extends a plurality of branches or vessels. For example, the device can be used in the external carotid artery and the common carotid artery to treat a stenosis located in the internal carotid artery. In contrast to balloon catheter-based devices, occlusion can be accomplished without necessitating the usage of devices, tools, or fluids that have to remain in the catheter of the device during the intervention. Because of this, the lumen of the catheter can serve as a guide for other instruments necessary for the intervention, such as interventional tools. This results in a catheter that has a relatively small outside diameter, e.g., about 7.5 French or less.

The elongate stretching member can have the shape of a catheter, a rod, a wire, or the like and can be guided within the lumen of the catheter of the device. By advancing the elongate stretching member axially in the distal direction within the catheter until it abuts a stop or receiving member operatively coupled to the catheter and then applying distal, axial force against the stop, a stretching of the first and second expandable areas in an axial direction of the catheter is accomplished which results in a reversal of the radial expansion (e.g., collapsed state). If the elongate stretching member is retracted proximally within the lumen of the catheter, the force imposed in the axial direction of the catheter is reduced and the self-expandable areas can naturally expand in the radial direction. Expansion in the radial direction also causes the length of the expandable areas to reduce or foreshorten. As the elongate stretching member can be removed from the catheter, the lumen of the catheter will be available for other usages, such as the insertion of one or more intervention tools. Another advantage of deploying the expandable areas by proximal retraction of the elongate stretching member is that the expandable areas, preferably two expandable areas, can be expanded substantially simultaneously. This means that the time for generating a blood flow desirable for the proximal protection during treatment of the carotid vessels is minimal, as the occlusion of the respective vessels can be generated in one rapid step.

In one aspect of the invention, the elongate stretching member has an inner lumen, in particular a lumen dimensioned for passage of a guidewire. A guidewire having a diameter of about 0.010 to 0.017 inches, and preferably about 0.013 to 0.015 inches is suitable for this purpose. The inner lumen can be configured to slidably accept such a guidewire by making the inner lumen diameter approximately 0.001 to 0.005 inches larger than that of the guidewire. This makes it possible to securely advance the elongate stretching member in an over-the-wire manner. The elongate stretching member can, for example, be a catheter or a hypotube. A hypotube is a hollow metal tube of very small diameter. These tubes, which are, inter alia, used for manufacturing hypodermic needles, have a longitudinal stiffness (high column strength) and a small wall thickness.

In another aspect of the invention, in the vicinity of the distal end of the inner lumen of the catheter, a receiving member is provided for receiving the distal tip of the elongate stretching member. The receiving member can be a tapered distal end of the inner lumen of the catheter. According to one embodiment, the receiving member extends proximally from the distal end of the inner lumen to at least the distal end of the expandable area provided nearest the distal end of the catheter (i.e., "the distal expandable area"). The receiving member can beneficially comprise an inner diameter that is tapered inwardly moving from the proximal to distal direction on the inner lumen of the catheter. Because the elongate stretching member that is inserted into the inner lumen of the catheter mainly serves the purpose of applying a force in the longitudinal direction towards the distal end of the catheter and thereby collapsing the expandable areas to the collapsed or non expanded state, it is sufficient to provide a receiving member for the elongate stretching member at the distal end of the distal expandable area. The distal tip of the catheter beyond the distal end of the distal expandable area can thus optionally be solid with only a lumen dimensioned for slidable passage of the guidewire (but not the elongate stretching member). In this way, a contact, abutment, or stopping face for the distal end of the elongate stretching member is provided and yet the catheter can still be inserted over a guidewire For example, a 0.015 inch diameter inner lumen would pass a 0.014 inch diameter guidewire but not a 0.016 inch diameter stretching member.

According to another embodiment, the receiving member extends from the distal end of the inner lumen to at or near the proximal end of a distal expandable area, preferably to the proximal end of the distal expandable area in its expanded state. In this alternative embodiment, the receiving member can be a rod, tube, or channel with a lumen dimensioned for passage of the guidewire. The rod, tube, or channel can be attached at the distal end of the catheter, i.e. only on the distal end of the rod, tube, or channel. Alternatively or additionally, the rod, tube, or channel can be attached at its outer diameter to the inner surface of the inner lumen of the catheter between the distal end of the distal expandable area and the distal end of the catheter.

By providing a receiving member that extends through the distal expandable area, the introduction of the elongate stretching member later during the intervention may be facilitated. As will be described later on in detail, the guidewire that is used for initial placement of the catheter can be withdrawn proximally from the distal end of the catheter. In this situation, an advancing of the elongate stretching member without the presence of the guidewire will be guided by the inner lumen of the catheter. In the region of the expandable area, however, an inner tubular shaped lumen may not be present. Because of this, the guiding of the elongate stretching member to the distal end of the inner lumen of the catheter may be difficult. By providing a receiving member extending to the proximal end of the distal expandable area, such a penetration of the elongate stretching member through the expandable area is not necessary. In addition, the overall distance over which the elongate stretching member has to be advanced to reach a position where the longitudinal stretching force can be applied to the catheter is reduced.

The receiving member can include or comprise a recess (e.g., an angled or tapered) at its proximal end for facilitating the receipt of the distal end of the elongate stretching member. The distal end of the elongate stretching member can have a profile that matches or mates with the recess of the receiving member. The recess can have, for instance, a cone shape to receive a tapered distal end of the elongate stretching member.

In another aspect of the invention, at least one expandable area of the catheter can include an inner and an outer component. The inner or outer component, or parts thereof, can be part of the catheter wall or body. If the inner component forms part of the catheter wall, it preferably only extends over part of the length of the expandable area. The remaining length of the inner component can be formed by a flexible member such as an elastic sheath. If the inner component is formed at least partially by the catheter material, the outer component can be a self-expandable element. The self-expandable element can be a braid, a mesh, a knit, a net, or the like. The proximal end of the self-expandable element can be attached to the outside of the catheter wall proximal to the portion of the catheter wall formed to which the flexible member (e.g., an elastic sheath) can be attached. The distal end of the self-expandable element can be attached to a proximal end of the catheter wall, which is attached to the distal end of the flexible member. In this case the self-expandable element can take the form of a tubular member (e.g., tube or the like). The outer component of the expandable area is radially self-expandable and preferably in a normal or expanded state in the absence of the presence of the elongate stretching member.

Alternatively or additionally, the inner component is a contraction member for axially contracting the expandable area. In this case, the inner component can be a spring, in particular a helical spring. The outer component of the expandable area of this embodiment can be the catheter wall or catheter body or a self-expandable element. If the outer catheter is formed by the catheter wall, one or more slits or other openings can be provided to allow radial expansion or buckling of the catheter wall in this area. If the outer component is a self-expandable element it can comprise a braid, mesh or a net.

Another alternative for actuating (e.g., expanding) the expandable areas can be due to a contraction force applied by an outer component or coating. In this case, a coating is provided over at least part of the expandable areas and induces an axially-oriented contraction force. In order to achieve such a contraction, the material such as a braid, net or mesh is covered in a state of maximal radial expansion, i.e. is covered, when it is axially compressed to the desired deployment diameter (e.g., ~20 mm for the proximal expandable area). When coating at least a part of the area in this axially compressed (and thus radially expanded state), the axial distance between adjacent elements, e.g. struts, is fixed by the coating. The coating material is preferably elastic material, such as silicone, polyurethane, or PTFE. If an expandable area at least partially coated with such coating is axially stretched and the stretching force is removed, the expandable area will return to the radially expanded state due to the contracting force applied by the coating on adjacent elements, such as struts.

Preferably, at least one of the expandable areas has openings in at least part of the expandable area. By providing openings, e.g. mesh openings, blood and particulate matter can enter into the inner volume of the expandable area and can be guided from there, for example via one or more holes, passageways, or ports in the inner component of the expandable area into the inner lumen of the catheter from where it can be transported to appropriate treatments, such as filters located external to the patient. Of course, the holes, passageways, or ports can also be located in other portion(s) of the catheter besides the inner component.

For filtering the collected blood and other fluid, the proximal end of the inner lumen of the catheter is at least temporarily connected to a collecting device, such as a container or bag and a filter can be provided at the inlet of the collecting device. The blood removed together with particles from the vessel can thus be separated from the particles and may be re-introduced into the body of the patient at a later stage.

In one aspect of the invention, the openings in the expandable area can additionally serve for permitting the passage of one or more intervention tools. Interventional tools can include, for example, a balloon catheter, stent catheter, or the like. If an inner component is provided in the expandable area, the inner component can also be provided with a respective opening.

In at least one of the first and second expandable areas, an outer component of the expandable area is preferably formed by a mesh, a net, a knit, or a braid. This embodiment is advantageous in that a homogeneous expansion of the expandable area can be ensured. In addition, the mesh, net, or braid structure also provides the holes or passageways through which fluid may flow so that the same can be directed proximally out of the catheter. In one aspect, the material being used for the self-expandable areas is made of a shape memory material. This can include a metal alloy such as, for instance, NITINOL. Alternatively, a spring material can be used to form the self-expandable areas.

According to one embodiment, in the proximally located expandable area, the size of the openings in the distal portion of the expandable area is larger than the size of the openings in the proximal portion of the expandable area. For example, the size of openings at the distal portion of the expandable area can be in the range of about 0.5 mm to about 5.0 mm and the size of the openings in the proximal portion can be smaller than about 1 mm. The distribution of sizes of the openings is preferable because, in one aspect, the proximal portion of the expandable area can be provided with a coating or cover while the distal portion can be left uncovered and can thus let blood and particles as well as intervention tools pass.

As explained above, at least a portion of the expandable areas can be partially or fully covered or coated in order to be able to use areas made of braid, mesh, or netting for occlusion of the blood vessel(s) of interest. The coating or covering is formed on or over the braid, mesh, or netting and closes the openings of the respective areas and prevents penetration of liquids, in particular of blood so as to form a substantially leak-free seal between the expandable area and the interior of the vessel.

According to one aspect, the proximally located self-expandable area is at least partially covered at the proximal end. For example, only about half of the length of the proximal expandable area (i.e., the proximal half), is covered. The distal portion of the proximally located self-expandable area is uncovered. The distally located, self-expandable area can be covered partially or completely.

The proximally located self-expandable area and the distally located self-expandable area can have the same or different sizes upon deployment. In one aspect, the distally located self-expandable area has a smaller diameter in the expanded state than the proximally located, self-expandable area in the expanded state.

According to one embodiment, the catheter is provided with at least one aperture in the catheter located between proximal end of the most proximal expandable area and the proximal end of the most distal expandable area. The at least one aperture can be provided between the two expandable areas or in the proximal expandable area. This aperture can be positioned on the side of the catheter tube or wall and can be generated by, for example, drilling, scraping, or cutting off the material of the catheter over a given length. The aperture offers the ability to bring intervention tools from within the lumen of the catheter to the site of intervention within the blood vessel without having to remove the catheter. The aperture offers a side port or access passageway for additional therapeutic devices. For example, the aperture allows the same catheter used to establish retrograde blood flow to also be used as the catheter for interventional tools, such as a balloon catheter or guidewire. The aperture can thus be provided in the wall of the catheter tube and/or within the expandable area and is dimensioned to allow passage of an intervention tool, e.g. a balloon catheter, therethrough.

It is desirable to allow for smooth guidance of the elongate stretching member and/or an intervention tool through and past an expandable area particularly when it is in its expanded state. Guiding can be provided by an inner component of the expandable area, such as a spring or part of the catheter tube and/or an elastic membrane. In particular, insertion through the proximal expandable area when expanded benefits from such an interior guide.

The interior guide, can for example, be formed by a flexible membrane sheath formed using, for example, an elastic material, which extends over at least part of the length of the expandable area. The interior guide can also, at least partially, be formed by a portion of the catheter tube or body. The length of the portion of the catheter tube extending into the expandable area should be dimensioned so that this portion of the catheter tube does not abut to the other end of the catheter tube on the other side of the expandable area when the area assumes the expanded state. In one aspect, the interior guide preferably has at least one hole or orifice that is in fluid communication with the lumen of the catheter. The at least one hole or orifice serves for removal of blood together with possibly particles into the catheter. In the case of a spring as being used as the inner component of the expandable area, the holes or orifices are formed by the distance between the spiral windings.

According to a further aspect of the present invention, a method for treating a vessel having a bifurcation area from which extends a plurality of branches includes inserting a catheter with at least two self-expandable areas for occlusion of vessels provided over the length of the catheter into a vessel, while an elongate stretching member is inserted within the lumen of the catheter to keep the expandable areas in a collapsed state. A distal expandable area is positioned distal to the bifurcation of the vessel in one of the branches, thereby positioning a proximal expandable area proximal to the bifurcation of the vessel. Upon retracting the elongate stretching member, the at least two expandable areas are urged to expand. The elongate stretching member can have a longitudinal stiffness greater than that of the first and second self-expandable areas.

While positioning the distal expandable area in one branch of the bifurcation an aperture can be positioned at or near the bifurcation. The aperture allows the passage of one or more intervention tools out through the catheter. The aperture can be located between the distal and proximal expandable area or in the proximal expandable area. For guiding the catheter to the intended position, a guidewire is normally inserted into the vessel before the insertion of the catheter and the elongate stretching member. In this regards, both the catheter and the elongate stretching member can be advanced in an over-the-wire arrangement.

After the removal of the elongate stretching member from the lumen of the catheter, the distal end of the guidewire will be retracted proximally until it reaches an aperture of the catheter distal to the proximal end of the proximally located self-expandable area and is advanced distally through the aperture into the other branch of the bifurcation. Thereby the guidewire will be brought into a position for guiding intervention tools such as a balloon catheter or balloon catheter. Consequently, it is not necessary to remove the guidewire completely from the catheter to introduce a different device. The exchange of the elongate stretching member and the intervention tool can be a rapid "over-the-wire" exchange. The distance over which a guidewire has to be advanced from the point of entry to the location of treatment is considerable, in particular for treatments of carotid vessels, where the devices will typically be inserted via the femoral artery. By avoiding the retraction and exchange of guidewires, the intervention time can be reduced considerably.

The distally located self-expandable area occludes the vessel of a branch distal to the branching position and blood flow is directed from the other branch toward the proximal expandable area in a retrograde manner. Preferably, the proximally located self-expandable area occludes the blood vessel proximal to the bifurcation and the blood flow passes through one or more openings provided in the proximally-locate self-expandable area into an interior portion of the self-expandable area. The blood flow then continues into the lumen of the catheter via one or more openings provided in the catheter or interior guide located within the proximally located self-expandable area. According to one embodiment, a medical instrument, e.g. a balloon catheter, balloon wire, or balloon catheter is inserted via the proximal end of the lumen of the catheter and guided to an aperture provided within the catheter wall. The medical instrument is inserted over the guidewire, and is guided out of the aperture and into the branch vessel to be treated.

For purposes of summarizing the invention, certain aspects, advantages and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein. These and other objects and advantages of the present invention will be more apparent from the following description taken in conjunction with the accompanying drawings.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements.

FIG. 1A illustrates a side view of a catheter according to one aspect of the invention.

FIG. 1B illustrates a cross-sectional view of the catheter of FIG. 1A taken along the line B-B'.

FIG. 1C illustrates a cross-sectional view of the catheter of FIG. 1A taken along the line C-C'.

FIG. 1D illustrates a cross-sectional view of the catheter of FIG. 1A taken along the line D-D'.

FIG. 2A is a side view of a catheter according to one embodiment. FIG. 2A illustrates the proximal and distal self-expandable areas in the collapsed state.

FIG. 2B illustrates a partially cut-way view of the proximal self-expandable area according to one embodiment.

FIG. 2C illustrates a partially cut-way view of the proximal self-expandable area according to another embodiment.

FIG. 5 illustrates a side view of a catheter according to another embodiment. The interior of a portion of the proximal self-expandable area is illustrated.

FIG. 6 illustrates a side view of a catheter according to another embodiment.

FIG. 13 illustrates the proximal and distal self-expandable areas in the collapsed configuration after the elongate stretching member has been re-introduced over the guidewire.

DETAILED DESCRIPTION OF THE ILLUSTRATED EMBODIMENTS

Figure 3A:
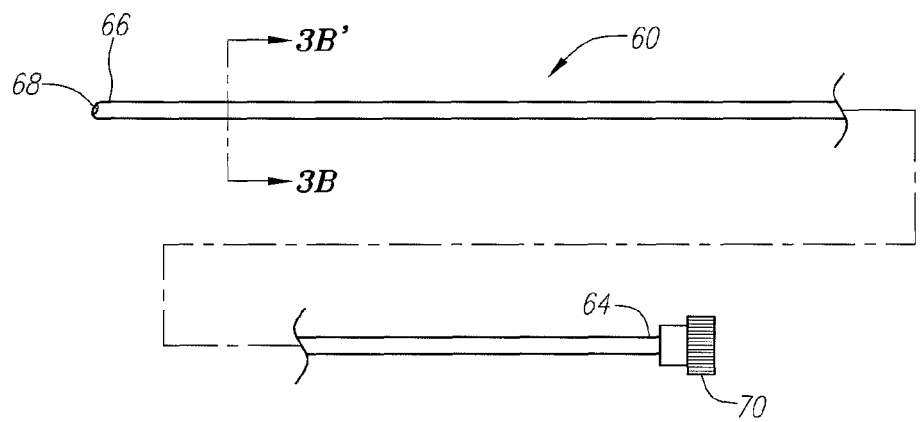
FIG. 3A illustrates an elongate stretching member according to one embodiment of the invention.

As used herein, the terms proximal and distal refer to a direction or a position along a longitudinal axis of a catheter or medical instrument. Proximal refers to the end of the catheter or medical instrument closest to the operator, while distal refers to the end of the catheter or medical instrument closest to the patient. For example, a first point is proximal to a second point if it is closer to the operator end of the catheter or medical instrument than the second point.

FIGS. 1A-1D, 2A-2C, 3A, 3B, and 4 illustrate various aspects of a system 10 for the protection of cerebral vessels or brain tissue. The system 10 includes a catheter 20 (illustrated in FIGS. 1A-1D), an elongate stretching member 60 (illustrated in FIGS. 1A, 3A and 3B), and a guidewire 80 (illustrated in FIG. 4). The system 10 can also include one or more additional components used during the interventional procedure. These include, for instance, an introducer or the like (not shown) that is used during introduction and placement of the catheter 20.

Referring to FIGS. 1A-1D, the catheter 20 is formed as an elongate member having a proximal end 22 and a distal end 24 and a lumen 26 extending therebetween. The catheter 20 includes an elongate body portion 28 that can incorporate a coiled and/or braided structure, or reinforcement, to impart sufficient axial compressive strength while at the same time providing the capability of the catheter 20 to bend through tortuous regions of the vasculature. In one aspect, the outer diameter of the catheter 20 is between about 3 French (F) to a maximal 10 F. However, in another aspect of the invention, the diameter falls within this range, for instance, the outer diameter ranging from between 4 F and 7 F. The length of the catheter 20 can be between about 60 cm and about 145 cm, with a preferable range between about 90 cm and 120 cm, although other lengths are contemplated to fall within the scope of the invention. As explained herein, one of the advantages of the system 10 is the ability to produce a very small device having a diminished size as compared to other devices.

In one embodiment, the lumen 26 extends fully from the proximal end 22 to the distal end 24. The lumen 26 can have varying or differing internal diameters depending on the particular location within the catheter 20. For example, as seen in FIGS. 1B and 1C, the diameter in the main body portion 28 of the catheter 20 can be substantially constant. In this portion, the diameter of the lumen 26 is generally determined by the dimensions of the interventional tool(s) being used and by the outer diameter of the catheter. Nonetheless, the inner diameter of the lumen 26 in this region generally falls within the range of about 3 F to about 7 F. In another aspect of the invention, the inner diameter of the lumen 26 in this region generally falls within the range of about 4 F to about 6 F. However, in one aspect of the invention, near the distal end 24 of the catheter 20 the diameter of the lumen 26 is reduced as illustrated in FIG. 1D. The diameter of the lumen 26 near the distal end 24 of the catheter 20 is dimensioned so as to permit passage of a guidewire 80 but not permit passage of the elongate flexible member 60. For example, the reduced diameter lumen 26 at or near the distal end 24 can have an inner diameter within the range of about 0.010 to 0.030 inches and preferably between 0.012 and 0.020 inches. In a preferred embodiment, for example, the reduced inside diameter of the lumen 26 near the distal end can be about 0.016 inches. Thus, a commonly used 0.014 inch diameter guidewire will pass through the lumen 26 and extend out the distal end 24 of the catheter 20, whereas a stretching member 60 having a diameter of 0.024 inches will not pass through the distal, reduced diameter portion of the lumen 26.

Figure 8:
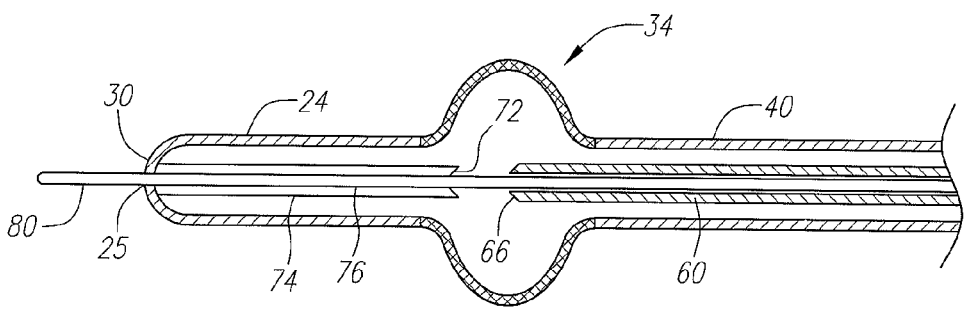
FIG. 8 illustrates a cross-sectional view of the distal end of a catheter according to another embodiment. The elongate stretching member and guidewire are illustrated therein.

Some, or all, of the inner surface of the lumen 26 may be coated or formed with a lubricious coating to improve the slidability of the elongate stretching member 60 or working instruments within the lumen 26 during use of the system 10. Of course, all or portions of the elongate stretching member 60 can optionally be coated with a lubricious coating such as coatings fabricated from polyurethane, silicone oil, other hydrophilic materials, or the like. In certain embodiments, the hydrophilic lubricious coating bond to the catheter 20 can be enhanced by plasma discharge treatment to roughen the surface of the catheter 20 and increase mechanical bond strength. Such plasma discharge treatment can be beneficial when the catheter 20 is fabricated from materials, such as polyethylene, polypropylene, polyester, polytetrafluoroethylene, and the like, that do not bond well to other materials. Referring to FIG. 1A and FIG. 8, the distal end 24 of the catheter can terminate in an atraumatic tip 30 that includes an opening 25 therein for passage of the guidewire 80. As seen in FIG. 1A, the catheter 20 is interrupted at two locations. At each interruption location is located a self-expandable area 32, 34. One self-expandable area is deemed a proximally located self expandable area 32 while the other self-expandable area is located distally with respect thereto and is deemed a distally located self-expandable area 34. Both self-expandable areas 32, 34 are configured to transition between a collapsed state and an expanded state. The interrupted areas are configured to permit longitudinal or axial movement of the distal ends of the self-expandable areas 32, 34, relative to the proximal ends of the self-expandable areas 32, 34. The collapsed state refers to a state in which the expandable areas 32, 34 comprise a minimum radius, diameter, or cross-sectional area. In the collapsed state, the self-expandable areas 32, 34 are substantially flush with the outer diameter of the catheter 20. In this regard, in the collapsed state, the self-expandable areas 32, 34 generally take a tubular-shaped configuration. FIG. 1A illustrates both self-expandable areas 32, 34 in a partially collapsed state so as to better illustrate various aspects of the system 10. Each expandable area 32 and 34 comprises a proximal end and distal end, which is affixed to the catheter shaft 20. The proximal end and the distal end of the expandable areas 32, 34 can be bonded, welded, or mechanically fixed to the catheter shaft 20.

In the expanded state, as described below, the self-expandable areas 32, 34 foreshorten along the longitudinal direction of the catheter 20 and form a spherical, elliptical, oblong, or cylindrical shape. The shape of the self-expandable areas 32, 34 is, however, not limited to the depicted shapes. The distal self-expandable area 34 can also, for example, have a cylinder shape, the shape of a funnel, a bowl, or of a plate. The deciding issue when choosing a particular deployment shape is that it is suitable for completely occluding the blood vessel, i.e. stop the blood flow, in the state, where the self-expandable area 32, 34 is expanded within the blood vessel. The perimeter of a partially, or fully, expanded self expandable area 32, 34 can be round or it can comprise a noncircular shape that conforms to an irregular vessel wall inner contour. Also the shape of the proximal self-expandable area 32 in the expanded state can be different from the depicted shape. For example, the proximal self-expandable area 32 area can have the shape of a sphere, an umbrella, or a plate. With the proximal self-expandable area 32 it is important that it is capable of occluding the blood vessel between the catheter 20 and the vessel wall in its expanded state. The proximal end and the distal ends of the expandable areas 32, 34 do not change their diameter even when the expandable areas 32, 34 are expanded and thus appear as tapered end regions on the expandable areas 32, 34.

In one aspect of the invention, the self-expandable areas 32, 34 are formed from a shape memory material. For example, the self-expandable areas 32, 34 can be formed from a shape memory alloy or metal such as NITINOL or other spring material such as stainless steel, cobalt nickel alloy, titanium, and the like. The self-expandable areas 32, 34 can be formed from a plastic or polymer such as polyester. The two self-expandable areas 32, 34 can be made of the same or, alternatively, different materials. In an embodiment where the self-expandable areas 32, 34 comprise NITINOL, the NITINOL can be superelastic or pseudoelastic in nature. In this embodiment, the austenite finish temperature is well below body temperature or even room temperature, causing the self expandable areas 32, 34 to possess strongly biased spring tendencies to expand laterally or radially outward from the longitudinal axis of the catheter 20.

In another embodiment, the self-expandable areas 32, 34 comprise shape-memory NITINOL, which has an austenite finish temperature above room temperature. In a preferred embodiment, the austenite finish temperature of the final self-expandable areas 32, 34 ranges between 25 to 35° C. and preferably between 28 and 33° C. In yet another embodiment, the self-expandable areas 32, 34 comprise shape memory NITINOL having an austenite finish temperature above body temperature such that external energy can be imparted to the self-expandable areas 32, 34 to generate the desired expansion. Such external energy can be in the form of Ohmic or resistive heating generated by electricity delivered through wires traversing the length of the catheter 20. Alternatively the energy can be imparted using methodologies such as, but not limited to, microwaves, radio-frequency energy, a hot balloon, high intensity focused ultrasound, and the like.

Figure 12:
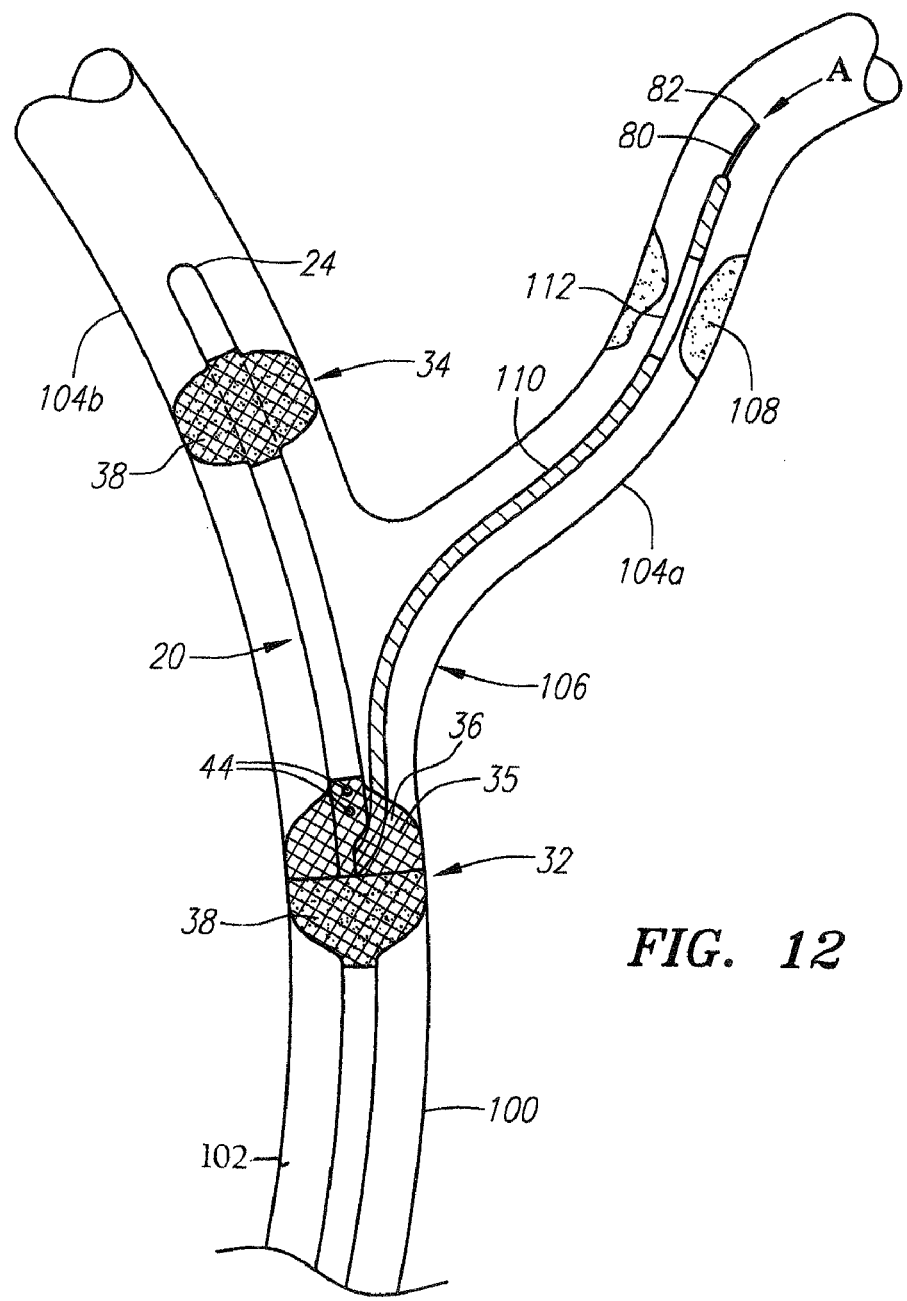
FIG. 12 illustrates the catheter of FIG. 11 with a working instrument being advanced over the guidewire for treatment of the stenosis.

The self-expandable areas 32, 34 can be configured as a mesh 35 as depicted in FIG. 1A. Of course, other configurations such as a braid, knit, weave, or netting can be used for the self-expandable areas 32, 34. As illustrated in FIG. 1A, at least a portion of the proximally located self-expandable area 32 includes a number of openings 36 located in the mesh 35. The openings 36 provide access for blood and potential particulate matter and other fluid to pass through during use of the system 10. The openings 36 can also be dimensioned to pass the guidewire 80 and interventional tool 110 as illustrated in FIG. 12. The mesh 35 (or other configuration) may have openings 36 that are regularly spaced and substantially uniform in size. Alternatively, the particular pattern or configuration of the openings may be varied or irregular. For example, with respect to the proximal self-expandable area 32, the distal portion of the mesh 35 may have larger cell openings 36 to better facilitate passage of the working instrument 110.

In one aspect of the invention, a portion of the proximally located self-expandable area 32 includes a cover 38. For example, the proximal portion of the self-expandable area 32 in FIG. 12 includes the cover 38 while the distal portion of the self-expandable area 32 is uncovered, thereby exposing the mesh 35 and openings 36 to the external environment. In one aspect, substantially the proximal half of the self-expandable area 32 is surrounded by the cover 38. In one embodiment, the distally located self-expandable area 34 can be fully covered by the cover 38. In another embodiment, however, only a distal portion of the distally located self-expandable area 34 can be surrounded by or enclosed by the cover 38. The cover 38 can be fabricated from a biocompatible flexible material that is substantially impermeable to fluids. Examples of materials suitable for use as the cover 38 include, but are not limited to, polytetrafluoroethylene, polyurethane, Hytrel, polyethylene, polyester, polyamide, polyimide, thermoplastic elastomer, silicone elastomer, and the like. The cover 38 can be separately manufactured and adhered or otherwise affixed to the mesh 35 on either the inside or the outside of the mesh 35. Alternatively, the cover 38 can be created by dipping, spraying, or other known applications. In this regard, the cover 38 can actually be a coating that is formed directly on the mesh 35. The cover 38 may be formed an interior surface of the mesh 35 or, alternatively, on an exterior surface of the mesh 35. The cover 38 can be manufactured as a fabric by weaving, braiding, knitting, or the like. In yet another embodiment, the fabric cover 38 can be coated with a polymeric coating or membrane as described above. The cover 38 can be affixed to the mesh 35 by adhesive bonding, welding, coating, attachment with mechanical fasteners, or the like.

In another embodiment, the portion of the self-expandable areas 32, 34 which are covered or otherwise coated with the cover 38 can be less than half of the length of the self-expandable areas 32, 34. The cover 38 only has to extend far enough to ensure the sealing or occluding of the end face formed in the expanded state between the catheter body 28 and the vessel wall, where this area abuts. The distal self-expandable area 34 can also only be partially covered although FIG. 1A illustrates a fully covered distal self-expandable area 34. For example, the distal portion of the self-expandable area 34 may be covered leaving the proximal portion uncovered. Alternatively, the entire distal self-expandable area 34 may be coated except for a plurality of filling holes that permit fluid passage to an interior portion. Also, here it should be ensured that the entire diameter of the blood vessel, into which the self-expandable area 34 is inserted, is covered to the inside of the vessel. A cover 38 or coating of only the upper or lower half can thus be sufficient to achieve full occlusion.

The size and ultimate shape of the self-expandable areas 32, 34 depend on the particular vessel(s) being treated. For example, the proximally located self-expandable area 32 may have a diameter of about 20 mm when expanded and may have a length of less than about 5 cm in the collapsed state. The distally located expandable area 34 can have a diameter of about 15 mm when expanded and can have a length of less than 3 cm in the collapsed state. In the collapsed state, both the proximal and distal self-expandable areas 32, 34 have outer diameters which substantially correspond to the outer diameter of the catheter 20 for a flush configuration. In addition, in the collapsed state, the length of the proximally located self-expandable area 32 is larger than the length of the distal self-expandable area 34. Of course, the dimensions described above are illustrative examples and diameters and lengths falling outside this ranges described above are contemplated to fall within the scope of the invention.

Still referring to FIG. 1A, the proximal and distal self-expandable areas 32, 34 are separated by an intermediate portion 40, which is formed by the body portion 28 of the catheter 20. The intermediate portion 40 thus separates the two self-expandable areas 32, 34. The length of the intermediate portion 40 can fall within the range of about 2 cm to about 15 cm or within a narrower range of about 5 cm to about 10 cm. As seen in FIG. 1A, the self-expandable areas 32, 24 include a hollow inner flexible member 41a, 41b disposed radially inward of the self-expandable mesh 35. For example, in the proximally located self-expandable area 32, the flexible member 41a is secured at one end to the intermediate portion 40 of the catheter and at the other end to the catheter body 28 which partially extends into the self-expandable area 32. The distally located flexible member 41b is secured at one end to the intermediate portion 40 and at the other end to the distal end 24 of the catheter 20.

The flexible members 41a, 41b can be formed from a membrane material or flexible tube having a lumen therein that is configured to permit passage of the elongate stretching member 60. The flexible members 41a, 41b are what enable the catheter 20 to lengthen when the elongate stretching member 60 is advanced within the lumen 26 of the catheter 20 to apply a tensioning force along the length of the catheter 20. The flexible members 41a, 41b serve as interior guides 48, 50, respectively, for the proximal and distal self-expandable areas 32, 34. The flexible members 41a, 41b can be secured to the outer mesh 35 instead of to the catheter 20 body.

Still referring to FIG. 1A, the catheter body 28 extends somewhat into the proximally located self-expandable area 32. An aperture 42 is provided that communicates with the lumen 26 of the catheter 26. The aperture 42 can be formed by scraping or cutting off the material of the catheter 26 over a given length to form a skived aperture 42. The aperture 42 is dimensioned to allow passage of one or more working instruments such as, for instance, a guidewire 80 and balloon catheter. The aperture 42 can be oriented or positioned adjacent to an uncovered portion of the mesh 35 in the proximally located expandable area 32. In this regard, the guidewire 80 and/or balloon catheter can be advanced along the main lumen 26 and out the aperture 42 so as to position the guidewire 80 and/or balloon catheter through the openings 36 in the mesh 35 and external to the device.

FIGS. 2A and 2B illustrate another embodiment of the catheter 20 in which the aperture 42 is located in the intermediate portion 40 between the proximal and distal self-expandable areas 32, 24. The aperture 42 extends over a given amount in the longitudinal direction of the catheter 20. The aperture 42 can also be configured to straddle a portion of the proximally located self-expandable area 32. In FIG. 2A, both self-expandable areas 32, 24 are illustrated in a collapsed state wherein their outer diameters are substantially equal to the outer diameter of the catheter 20. FIG. 2B illustrates a cut-away view of the internal aspect of the proximally located self-expandable area 32. In this embodiment, the catheter body 28 extends over the proximal end of the self-expandable area 32 and into the self-expandable area 32 to form part of an interior guide 48. In the portion 46 of the catheter body 28 that extends into the self-expandable area 32, a plurality of holes 44 are disposed that provide access to the interior lumen 26. At the end of the catheter portion 46, a flexible member 41a in the form of a membrane sheath is attached. In the depicted embodiment, the membrane sheath 41a extends to the distal end of the proximal self-expandable area 32. There the membrane sheath 41a can be attached to the catheter body 28, which forms the intermediate area 40. Alternatively, the membrane sheath 41a can be attached to the material (e.g., mesh 35), which forms outer component of the self-expandable area 32. A similar interior guide 50 can be located within the distally located self-expandable area 34 as illustrated in FIG. 2C. This particular interior guide 50 can have a similar layout as the interior guide 48 within the proximal self-expandable area with the exception that there are no openings in the catheter body 28 extending into the distal self-expandable area 34.

Referring back to FIG. 1A, one or more holes 44 are provided in the catheter 20 to provide an access pathway to inside the lumen 26 of the catheter 20. The holes 44 can be disposed inside the proximally located self-expandable area 32. Blood with potential particulate matter is able to flow into the lumen 26 of the catheter 20 via the access holes 44 which can be populated about the periphery of the catheter 20. FIG. 2B illustrates an alternative embodiment of the catheter 20 illustrating the plurality of holes 44 disposed within the interior guide 48 portion. Generally, the holes or orifices 44 may be located in the most proximate portion of the self-expandable area 32 so as to prevent the accumulation of debris proximate to the holes 44. The holes or orifices 44 may be populated around the periphery of the catheter 20. The number of holes or orifices 44 and their diameters is such that the combined cross-sectional area of all the holes 44 is at least as great as the cross-sectional area of the lumen 26 of the catheter 20.

Figure 3B:
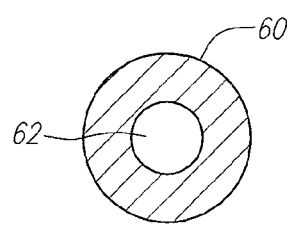
FIG. 3B illustrates a cross-sectional view of the elongate stretching member taken along the line B-B' of FIG. 3A.

FIGS. 1A, 3A, and 3B illustrate an elongate stretching member 60 that is used as part of the system 10. The elongate stretching member 60 is an elongate member that is configured to slide within with lumen 26 of the catheter 20. In this regard, the elongate stretching member 60 is removable from within the catheter 20 to selectively expand or contract the self-expandable areas 32, 34 based on the presence or absence within the lumen 26. The elongate stretching member 60 includes a lumen 62 (shown in FIG. 3B) that is configured to receive a guidewire 80 as explained in more detail below. The lumen 62 preferably traverses the entire length of the elongate stretching member 60 from a proximal end 64 to a distal end 66. The distal end 66 of the elongate stretching member 60 advantageously includes a hole 68 located at or near the tip such that the guidewire 80 can pass for deployment of the system 10. The proximal end 64 of the elongate stretching member 60 includes a locking member 70 that is configured to mate with a proximal hub 52 of the catheter 20.

The locking member 70 is advantageously located a fixed distance away from the distal end 66 such that when the elongate stretching member 60 is fully inserted into the lumen 26 of the catheter 20 and the proximal and distal self-expandable areas 32, 34 are collapsed as shown in FIG. 2A, the locking member 70 is able to be secured to the proximal hub 52. In this regard, the locking member 70 secures or otherwise locks the relative position between the catheter 20 and elongate stretching member 60 to maintain the first and second self-expandable areas 32, 34 in the tensioned, collapsed state.

The locking member 70 can be secured to the proximal hub 52 via threads or the like. For instance, the proximal hub 52 can include a Luer lock fitting, a threaded fitting, a snap-lock fitting, or the like. In addition, the locking member 70 preferably incorporates a seal between the proximal hub 52 and the elongate stretching member 60 so that blood or other fluid does not flow retrograde out the proximal end 22 of the catheter 20. For example, the locking member 70 can include a hemostasis valve, e.g. pinhole or duckbill valve, or a combination thereof, or a Tuohy-Borst type cap.

The elongate stretching member 60 can be a tube or a rod with the central lumen 62 extending over the length thereof. For example, the elongate stretching member 60 can be formed from a catheter or hypotube. The elongate stretching member 60 should be of sufficient flexibility in order to be inserted into the lumen 26 of the catheter 20. On the other hand, the elongate stretching member 60 should be provided with sufficient stiffness to stretch the catheter 20, in particular, the self-expandable areas 32, 34 when fully inserted into the catheter 20. Thus, the elongate stretching member 60 should have a longitudinal stiffness greater than that of the self-expandable areas 32, 34. The stretching process is performed by advancing the elongate stretching member 60 into to the distal end 24 of the lumen 26 of the catheter 20. Once the elongate stretching member 60 has reached this position and abuts either directly or indirectly the distal end 24 of the catheter 20, the catheter 20 can be stretched by applying an additional pushing force in the longitudinal direction of the elongate stretching member 60. The elongate stretching member 60 can then be temporarily affixed at the proximal hub 52 of catheter 20 using the locking member 70 in order to generate a sufficient and constant stretching force to maintain the collapsed configuration.

By retracting the elongate stretching member 60 from the distal end 24 of the catheter 20, the pressure in the longitudinal direction of the catheter 20 is removed and the proximal and distal self-expandable areas 32, 34 can then expand into their "natural," expanded state. By removing the stretching force, the self-expandable areas 32, 34 then transition into their energetically favorable, expanded state, which is utilized for vessel occlusion. The elongate stretching member 60 is removed completely from the catheter 20. As can be seen from FIG. 10, the distal self-expandable area 34 is completely covered with the cover 38 and has the shape of a sphere or ball. The proximal self-expandable area 32, in contrast, is only covered with the cover 38 at its proximal half, leaving the distal half formed by the mesh 35 to permit fluid infiltration. The proximal self-expandable area 32 generally has a greater length than the distal self-expandable area 34 and in addition is generally in the shape of a cylinder.

Figure 4:
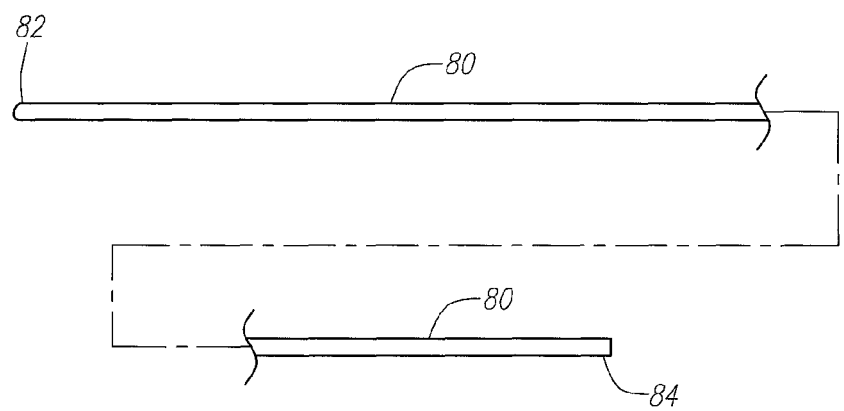
FIG. 4 illustrates a guidewire according to one embodiment.

FIG. 4 illustrates a guidewire 80 that is used in connection with the system 10. The guidewire 80 has a distal end 82 and a proximal end 84. The guidewire 80 is a conventional guidewire 80 that is dimensioned such that it can pass through the lumen 62 of the elongate stretching member 60. The guidewire 80 is advantageously a "rapid exchange" type guidewire such that elongate stretching member 60 and the catheter 20 can be advanced over the proximal end 84 of the guidewire 80 and advanced distally into position.

FIG. 5 illustrates an alternative embodiment of a catheter 20. In this embodiment, at least one of the self-expandable areas 32, 34 includes a spring 54 as the inner guide 48. The spring 54 is affixed at a proximal end to the catheter body portion 28 or shaft. The distal end of the spring 54 is affixed to the intermediate portion 40 of the catheter 20. The spring 54 applies a contraction force on the outer mesh 35, which causes the same to expand into the expanded or deployed state as illustrated in FIG. 5. While the outer component of the self-expandable area 32 is illustrated as a mesh 35 it should also be understood that the outer component can include a braid or net. In this embodiment, only a proximal portion of the mesh 35 is covered with the cover 38. The distal portion of the mesh 35 remains open via holes 36 to allow blood and other fluid to flow into the self-expandable area 32. In this embodiment, there is no need for holes to be provided in the catheter 20 to permit blood flow to enter the lumen 26. Rather, blood or other fluid in the interior of the self-expandable area 32 may just enter the lumen 26 directly.

The spring 54 thus provides the biasing or contraction force to move the self-expandable area 32 into the deployed state. The spring 54 also serves as the interior guide 48 for the elongate stretching member 60. In this regard, the spring 54 is configured to permit passage of the elongate stretching member 60 through the interior portion of the spring 54. The proximal and distal self-expandable areas 32, 34 can be collapsed by extending the elongate stretching member 60 through the lumen 26 of the catheter 20 and extending or stretching the self-expandable areas 32, 34. The spring 54, given its flexible nature, expands when subject to this stretching force, thereby allowing the self-expandable area 32 to transition to the collapsed state. The spring 54 can by formed from a metallic or polymer-based material. For example, the spring 54 can be formed from NITINOL or a plastic or polymer such as polyester. While FIG. 5 illustrates the aperture 42 being located in the intermediate portion 40 of the catheter 20 it should be understood that the aperture 42 can be located within or straddle the self-expandable area 32.

FIG. 6 illustrates yet another embodiment of a catheter 20. In this embodiment, the outer component of the self-expandable areas 32, 34, which can include a mesh 35, braid, or net is covered with a coating of elastic material 56. When the self-expandable areas 32, 34 are covered or otherwise coated with the elastic material 56, the self-expandable areas 32, 34 assume their deployed or expanded state as illustrated in FIG. 6. The elastic material 56 can include silicone, polyurethane, or PTFE. A biasing or stretching force must then be applied to the self-expandable areas 32, 34 to decrease their respective diameters to assume the collapsed state. The coating of elastic material 56 can be applied during manufacture of the self-expandable areas 32, 34. For example, the coating of elastic material 56 can be applied to the self-expandable areas 32, 34 when they are in the deployed or expanded state. The elastic material 56 will then retain this configuration by encapsulating or securing the underlying mesh 35 or other material forming the outer component.

The collapsed state can be achieved by insertion of the elongate stretching member 60 into the lumen 26 of the catheter 20 and advancing the same until the distal end 24 is reached to apply a stretching force to move the self-expandable areas 32, 34 axially distally, thus resulting in diametric or radial collapse of the self-expandable areas 32, 24. The elongate stretching member 60 utilizes a construction having high column strength. The coating of elastic material 56 can be separately manufactured and adhered or otherwise affixed to the mesh 35 or underlying support structure. Alternatively, the coating of elastic material 56 can be created by dipping, spraying, or other known applications.

As seen in FIG. 6, the coating of elastic material 56 covers all of the distally located self-expandable area 34. In contrast, a portion of the proximally located self-expandable area 34 is devoid of the coating of elastic material 56. For example, one or more holes or apertures 58 can be provided in the coating of elastic material 56 to permit blood and other fluid to enter the interior portion of the self-expandable area 32. Once inside, the blood or other fluid may enter the main lumen 26 as described herein with respect to the other embodiments. This may include holes located within an interior guide 48 or elsewhere on the catheter 20. Alternatively, the blood or other fluid may enter directly into the lumen 26 of the catheter 20.

Figure 7A:
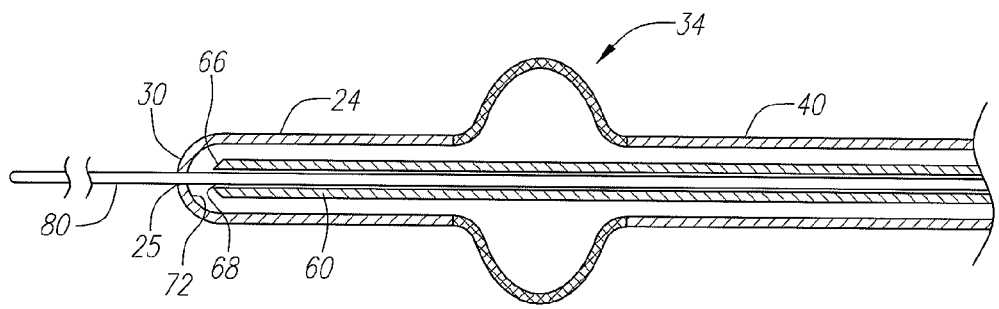
FIG. 7A illustrates a cross-sectional view of the distal end of a catheter according to one embodiment. The elongate stretching member and guidewire are illustrated therein.

Referring now to FIG. 7, a cross-sectional view of the distal end 24 of a catheter 20 is illustrated according to one embodiment of the invention. As seen in FIG. 7, the distal end 24 of the catheter 20 includes a hole 25 dimensioned to permit passage of the guidewire 80 but not the elongate stretching member 60. In this regard, a receiving surface 72 is formed on the interior portion of the catheter 20 that is configured to abut with the distal end 66 of the elongate stretching member 60. During use, the elongate stretching member 60 is advanced down the lumen 26 of the catheter 20 until the distal end 66 of the elongate stretching member 60 contacts the receiving surface 72. Once contact is made, additional advancement of the elongate stretching member 60 causes at least partial stretching of the self-expandable areas 32, 34 such that the self-expandable areas 32, 24 so that these are collapsed in a state like that illustrated in FIG. 2A. In FIG. 7A, the distal end 66 of the elongate stretching member 60 is disposed away from the receiving surface 72 and, hence, the distally located self-expandable area 34 is shown in the expanded or deployed configuration.

Figure 7B:
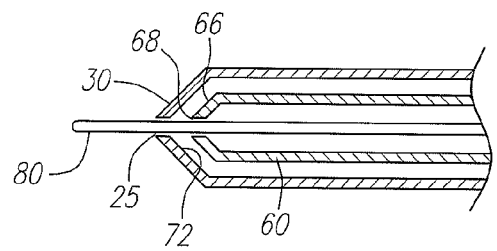
FIG. 7B illustrates a cross-sectional view of the distal tip of a catheter according to another embodiment. The elongate stretching member and guidewire are illustrated therein.

It should be understood that the receiving surface 72 does not have to be located at the distal most end of the catheter 20 as illustrated in FIG. 7A. For example, the interior portion of the catheter 20 that is located distal to the self-expandable area 34 can be partially or completely solid (except for the hole 25 for the guidewire 80) to form a receiving surface 72 that is located at or distal to the self-expandable area 34. FIG. 7B illustrates another embodiment of a catheter 20 in which the receiving 72 surface is shaped in the form of a taper or the like. The distal end 66 of the elongate stretching member 60 also is shaped to include a corresponding tapered surface to form a mating configuration when the elongate stretching member 60 contacts or abuts the receiving surface 72 (the tapering angles of both the receiving surface 72 and the distal end 66 are substantially the same). While a taper or angled surface is illustrated, other configurations can also be employed.

FIG. 8 illustrates yet another embodiment of a catheter 20. In this embodiment, the catheter 20 incorporates a receiving member 74 located at least partially at the distal end 24 of the catheter. The receiving member 74 extends proximally within the catheter 20 and terminates at a receiving surface 72 that is configured to receive the distal end 66 of the elongate stretching member 60. The receiving member 74 includes a lumen 76 therein that communicates with the hole 25 located at the distal tip of the catheter 20. The lumen 76 is sized to permit passage of the guidewire 80 but not permit passage of the elongate stretching member 60. The receiving surface 72 can be tapered (e.g., configured as a cone) or otherwise configured to engage with the distal end 66 of the elongate stretching member 60. In one aspect, the receiving member 74 extends proximally to at least the distal end of the self-expandable area 34. Of course, the actual point of termination of the receiving surface 72 may vary. For example, the receiving member 74 can terminate at a proximal end or region of the distally located self-expandable area 34.

The receiving member 74 can include a rod, tube, or channel that is bonded or otherwise affixed within the catheter 20. The receiving member 74 can be secured at the distal end to the distal end 24 of the catheter. Alternatively, or additionally, the receiving member 74 can be secured at its outer diameter or outer surface to the inner surface of the inner lumen 26 of the catheter 20. FIG. 8 illustrates the distally located self-expandable area 34 in the expanded state because the elongate stretching member 60 is located proximal with respect to the receiving member 74. In order to collapse the self-expandable area 34, the elongate stretching member 60 is advanced in the distal direction until the distal end 66 engages with the receiving surface 72 of the receiving member 74. After contact, additional distal displacement of the elongate stretching member 60 at least partially stretches the self-expandable areas 32, 34 into their collapsed state. Conversely, when the elongate stretching member 60 is retracted proximally from the catheter 20, the self-expandable areas 32, 34 transition back to their expanded state.

Figure 15A:
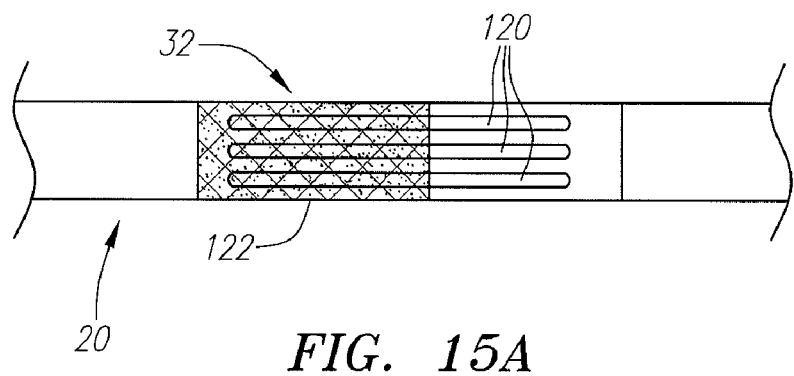
FIG. 15A illustrates a proximal self-expandable area according to one embodiment of the invention. The self-expandable area is illustrated in the collapsed state.
Figure 15B:
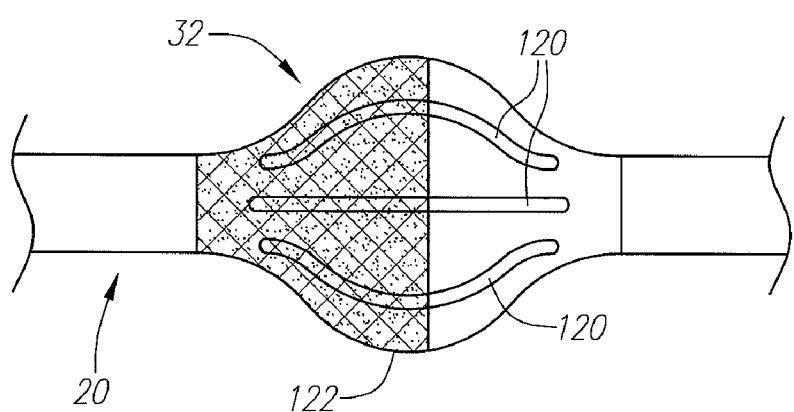
FIG. 15B illustrates the proximal self-expandable area of FIG. 15B. The self-expandable area is illustrated in the expanded state.

FIGS. 15A and 15B illustrate a catheter 20 according to another embodiment of the invention. In this embodiment, the construction of the catheter 20 is made into the self-expandable area 32, 34. FIG. 15A illustrates a proximally located self-expandable area 32 that includes a plurality of slots 120 formed in the wall of the catheter 20. The slots 120 allow the buckling of the catheter 20 into the deployed state of FIG. 15B. The self-expandable area 32 is in the collapsed state because of the insertion of the elongate stretching member 60 (not shown). A portion of the slots 120 are covered via a cover 122 that forms a barrier for fluids. In this regard, the cover 122 forms the seal between the interior surface of the vessel and the catheter 20 when the self-expandable area 32 is in the expanded state as shown in FIG. 15A. The cover 122 may be formed from an elastic material that optionally aids in expanding the self-expandable area 32. The slots 120 may be dimensioned to permit passage of a working instrument 110. Similarly, the slots 120 permit body fluids such as blood to communicate with an interior lumen (not shown) of the catheter 20 so that the blood and other fluid may withdrawn via the catheter 20 as explained herein.

After retraction of the elongate stretching member 60, the self-expandable area 32 expands outward in the radial direction as illustrated in FIG. 15B. This portion of the catheter body may be constructed from a segment that is biased to expand into this configuration in the absence of the stretching force. Of course, the elastic material of the cover 122 may also assist in the transition of the self-expandable area 32 to the state illustrated in FIG. 15B.

Figure 9:
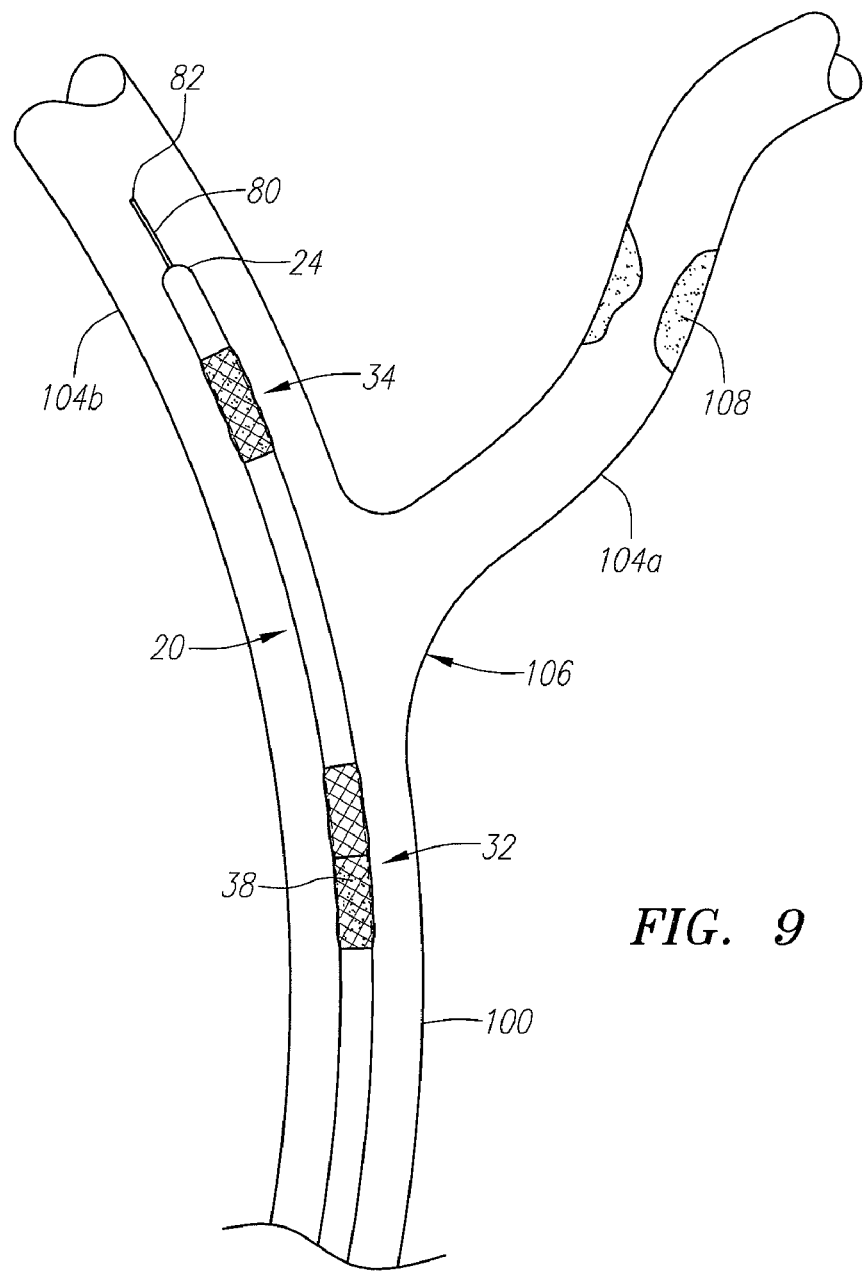
FIG. 9 illustrates the catheter being positioned within branch vessel of a bifurcation. The illustrated branch vessel that contains the catheter is the external carotid artery.

FIGS. 9-13 and 14A-14F illustrate use of the system 10 according to one aspect of the invention. FIG. 9 illustrates a bifurcated vessel 100 that includes a common vessel 102 and a plurality of branch vessels 104a, 104b. The branch vessels 104a, 104b branch from the common vessel 102 at a bifurcation 106. In one aspect of the invention, the vessels 102, 104a, 104b include cerebral vessels. For example, the common vessel 102 may include the common carotid artery while branch vessel 104a is the internal carotid artery and branch vessel 104b is the external carotid artery. As seen in FIGS. 9-12, a stenosis 108 or narrowing of the internal carotid artery 104a is shown that is treated with the system 10.

Figure 14A:
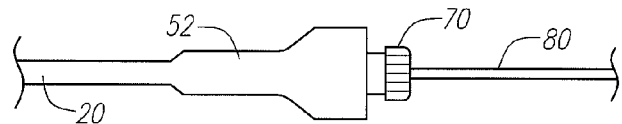
FIG. 14A illustrates the proximal end of the catheter along with the elongate stretching member being locked or fixed with respect to the catheter. The guidewire is shown exiting the proximal hub of the catheter.

Initially, a guidewire 80 is introduced to the subject, typically through the femoral artery and is advanced until a distal end 82 reaches the external carotid artery 104b. Once the guidewire 80 is advanced in place, the catheter 20 is then inserted into the body over the guidewire 80. In this regard, the catheter 20 is advanced over the proximal end 84 of the guidewire 80 and is advanced distally. The catheter 20 is advanced and positioned in the collapsed state as illustrated in FIG. 9. Specifically, both the proximal and distal self-expandable areas 32, 34 are collapsed down as illustrated due to the stretching of the catheter 20 via the elongate stretching member 60 that is disposed inside the lumen 26 of the catheter 20. FIG. 14A illustrates the elongate stretching member 60 being inserted in the proximal end of the catheter 20. FIG. 14A also illustrates the locking member 70 that is secured to the proximal hub 52 of the catheter 20. The locking member 70 ensures that the proximal and distal self-expandable areas 32, 34 remain in the collapsed state.

Figure 14B:
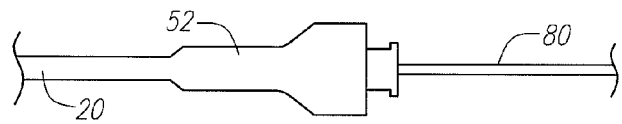
FIG. 14B illustrates the proximal end of the catheter after removal of the elongate stretching member. The guidewire is shown exiting the proximal hub of the catheter.

The catheter 20 is then advanced beyond the common carotid artery 102 and the distal end 24 is introduced into the external carotid artery 104b. Once the distal end 24 is advanced a sufficient distance distal relative to the bifurcation 106, the elongate stretching member 60 is withdrawn proximally relative to the catheter 20. This may include, for example, unscrewing the locking member 70 from the proximal hub 52 and withdrawing the elongate stretching member 60 in the proximal direction. FIG. 14B illustrates the removal of the elongate stretching member 60 from the catheter 20. As the elongate stretching member 60 is withdrawn, the proximal and distal self-expandable areas 32, 24 expand substantially simultaneously as illustrated in FIG. 10.

Figure 10:
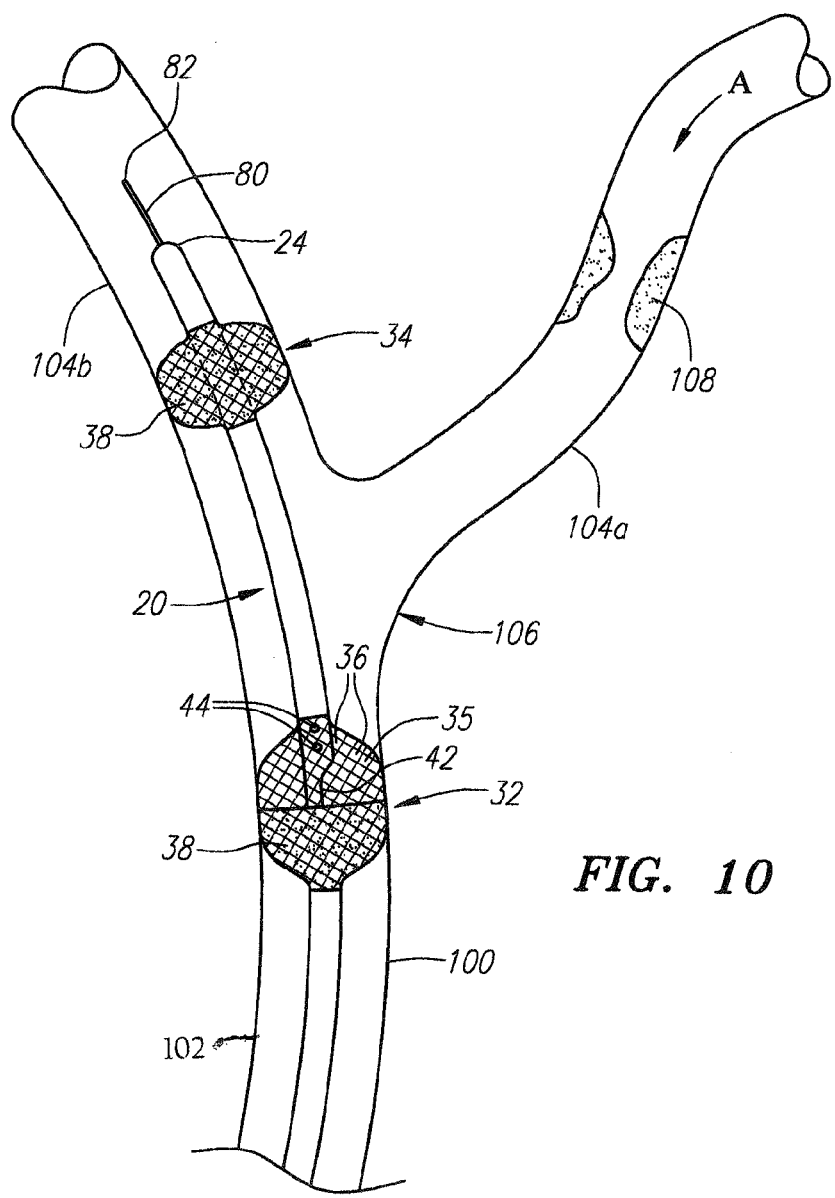
FIG. 10 illustrates the catheter of FIG. 9 wherein the proximal and distal self-expandable areas are expanded or deployed to occlude blood flow in the external carotid artery and the common carotid artery.

As seen in FIG. 10, because the distal self-expandable area 34 is covered at least on its distal side (FIG. 10 illustrates the distal self-expandable area being fully covered), the blood stream which is present within the common carotid artery 102 can no longer flow towards the external carotid artery 104b. At the same, the proximal self-expandable area 32 is deployed in the expanded state. Because of the additional occlusion of the common carotid artery 102, the blood flow in the internal carotid artery 104a is reversed from antegrade flow to retrograde flow in the direction of arrow A and is thus directed toward the common carotid artery 102. This "reversed" blood flow then enters the interior of the proximal self-expandable area 32 via the openings 36 in the mesh 35 and then passes into the inner lumen 26 of the catheter 20 via the holes 44. The cover 38 on the proximal self-expandable area 32 forms a sealing configuration with the internal walls of the vessel 102. The occlusion of the respective vessels 102, 104b can be tested by flushing radiographic contrast media into the vessels 102, 104b and observing the image using fluoroscopy or X-ray visualization equipment. Magnetic resonance angiography (MRA) can also be used to evaluate blood vessel patency.

Still referring to FIG. 10, after passing the mesh 35 (or net or braid), the blood or other fluid enters into the lumen 26 of the catheter 20 via the holes 44 of the catheter body 28. The proximal portion of the self-expandable area 32 that includes the cover 38 serves as a funnel for guiding or directing the blood stream into the lumen 26 of the catheter 20. Due to the reversal of blood flow direction from normal antegrade flow to reverse retrograde flow, the treatment of a stenosis 108 located within the internal carotid artery 104a can now be performed without hesitation.

Figure 11:
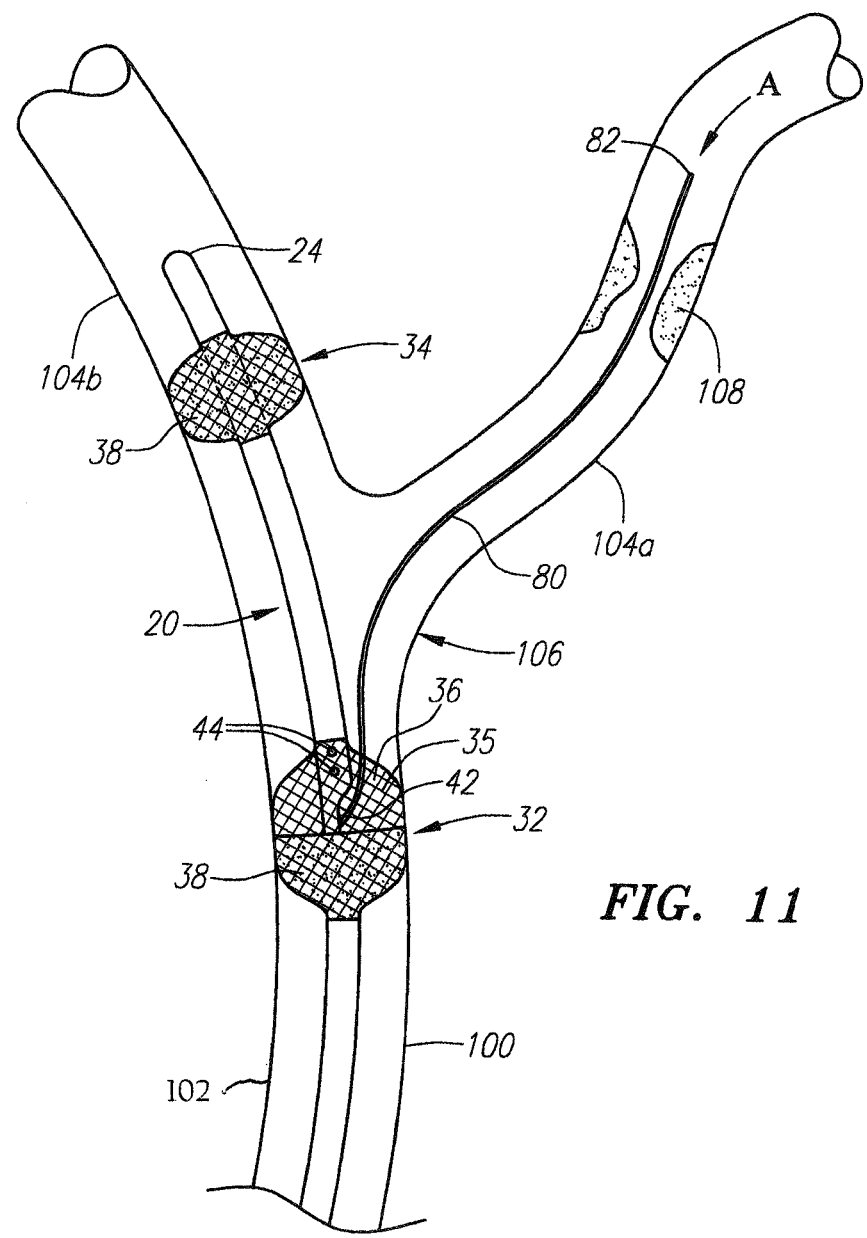
FIG. 11 illustrates the catheter of FIG. 10 wherein the guidewire has been first retracted proximally and then advanced distally into the internal carotid artery that contains a stenosis.
Figure 14C:
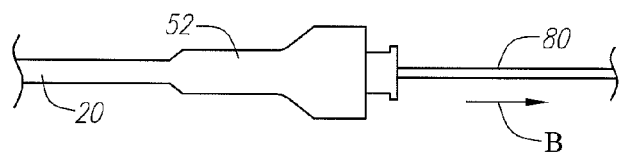
FIG. 14C illustrates proximal retraction of the guidewire relative to the catheter.
Figure 14D:
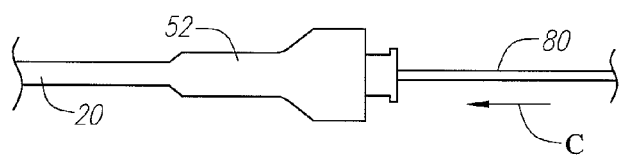
FIG. 14D illustrates distal advancement of the guidewire relative to the catheter.

With reference to FIG. 11, the treatment procedure continues with the guidewire 80 being retracted proximally within the catheter 20 until the distal end 82 of the guidewire 80 reaches the location of an aperture 42, which is provided at the side of the catheter 20. FIG. 14B illustrates proximal movement of the guidewire 80 in the direction of arrow B. While FIG. 11 illustrates the aperture 42 located within the proximal self-expandable area 32 it should be noted that the aperture 42 can be located within the intermediate portion 40 of the catheter 20 or even straddle the proximal self-expandable area 32. At this position the guidewire 80 is then advanced distally to pass through the aperture 42 and out of the self-expandable area 32. FIG. 14C illustrates distal movement of the guidewire 80 relative to the catheter 20 in the direction of arrow C. In this regard, the guidewire 80 can pass through one of the openings 36 formed in the mesh 35 of the self-expandable area 32. As seen in FIG. 11, the guidewire 80 is further advanced to enter into the internal carotid artery 104*a* and reach and/or cross the stenosis 108.

Figure 14E:
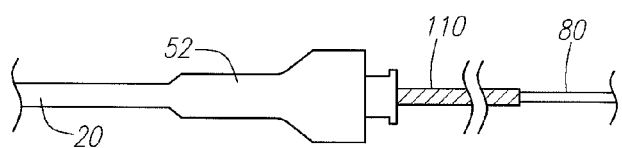
FIG. 14E illustrates the proximal end of the catheter along with an interventional tool being advanced over the guidewire.

With reference to FIGS. 12 and 14E, one or more intervention tools 110 can now be inserted via the lumen 26 of the catheter 20 over the guidewire 80. The interventional tool 110 can include a balloon catheter or stent catheter having an expandable member 112 thereon. The expandable member 112 can inflate to open or widen the stenosis 108. Alternatively, an interventional device such as a stent, atherectomy device, or the like (not shown) can be deployed within the stenosis 108 by the interventional tool 110. In one aspect of the invention, an interior guide 48 is provided within the proximal self-expandable area 32. The interior guide 48 enables the intervention tool 110 to be brought to the desired location without hitting the transition of the self-expandable area 32 to the intermediate region 40.

Because the retrograde or reverse direction of blood flow generated by the deployed self-expandable areas 32, 34 any particulate matter, such as thrombosis, atheroma, or the like, which may detach or slough off from the stenosis 108 during the treatment will be transported in the direction of arrow A toward the proximal self-expandable area 32 from where they can be removed via the lumen 26 of the catheter 20. The blood or other fluid that may contain particulate matter can then be filtered or treated and reintroduced to the patient. For example, the blood can be subject to filtration and then introduced into the patient's venous system.

Figure 13:
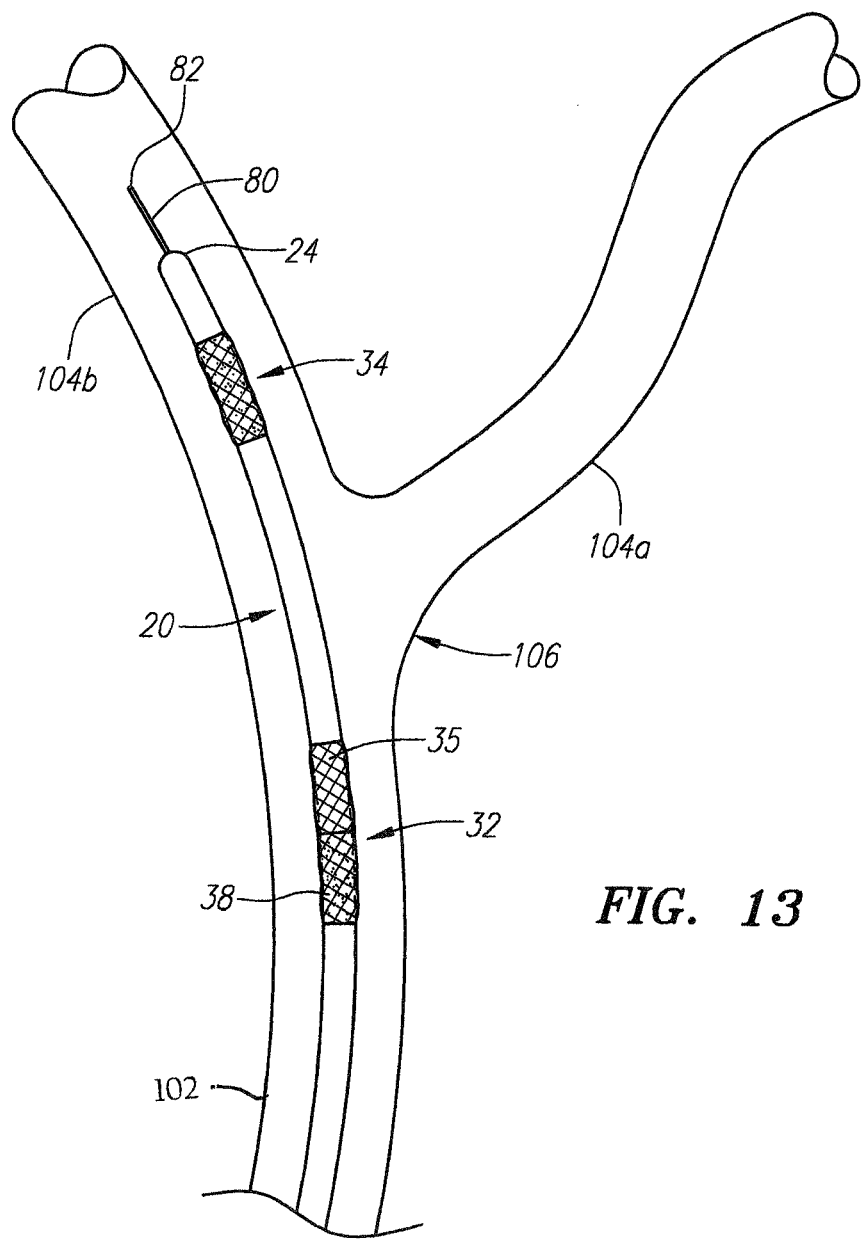
FIG. 13 illustrates the catheter of FIG. 12 with the working instrument withdrawn. In addition.
Figure 14F:
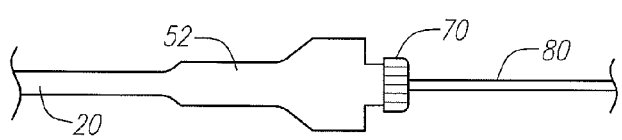
FIG. 14F illustrates the proximal end of the catheter along with the elongate stretching member after the elongate stretching member has been re-introduced over the guidewire and into the lumen of the catheter to collapse the proximal and distal self-expandable areas.

FIGS. 13 and 14F illustrate the system 10 after the interventional tool 110 has been retracted proximally from the catheter 20. In addition, FIGS. 13 and 14F illustrate the re-introduction of the elongate stretching member 60 over the guidewire 80. The elongate stretching member 60 is advanced over the guidewire 80 until the distal end 82 of the guidewire 80 contacts the receiving surface 72 of the catheter 20. Additional distal advancement of the elongate stretching member 60 then stretches the proximal and distal self-expandable areas 32, 34 into their collapsed state as seen in FIG. 13. In addition, the elongate stretching member 60 can be secured to the proximal hub 52 of the catheter 20 via the locking member 70. The catheter 20 and guidewire 80 can then be withdrawn proximally and ultimately removed from the subject. As shown in FIG. 13, the former stenosis 108 is now gone (or reduced) after treatment with the interventional tool 110.

While the method described above has been mainly described with regards to the treatment of carotid vessels it should be understood that the invention can be applied to other vessels, in particular, the treatment of one or more branches of a bifurcated vessel. Because the invention permits access to a blocked region between two expanded areas, it can also be applied to other tubular vessels where the treatment site is located between the two expanded areas.

The above-described system 10 is easier to use than prior systems because a single device employs both proximal and distally located occlusive elements that can be simultaneously deployed simply by retraction of the elongate stretching member 60. The system 10 avoids the need for separate inflation lumens and can thus be made with a relatively small cross sectional area (e.g. 7 F or less). The system 10 is also advantageous because a single guidewire 80 can be used to both positioning of the catheter 20 as well as the interventional tool(s) 110. Normal or antegrade flow in the patient can be quickly re-established in the patient simply by insertion of the elongate stretching member 60 over the pre-placed guidewire 80. Finally, conventional imaging techniques can be used to view the entire interventional procedure using the system 10 described herein.

While embodiments of the present invention have been shown and described, various modifications can be made without departing from the scope of the present invention. The invention, therefore, should not be limited, except to the following claims, and their equivalents.

What is claimed is:

1. A method for treating a defect in bifurcated vasculature having a common blood vessel and at least first and second branch blood vessels, said method comprising the steps of:
   A) providing or obtaining a system that comprises;
      i) an elongate, flexible catheter having a proximal expandable area, a distal expandable area, an elongate member receiving lumen, and a treatment device outlet opening, said proximal expandable area being self-expandable from an elongated radially collapsed configuration to a large diameter expanded configuration, said distal expandable area being self-expandable from an elongated radially collapsed configuration to a large diameter expanded configuration; and
      ii) an elongate member having a guidewire lumen extending longitudinally therethrough, said elongate member being is a) insertable into the elongate member receiving lumen, b) advanceable to a distal position whereby it engages a portion of the elongate flexible catheter and causes both the proximal and distal expandable areas to assume elongated radially collapsed configurations and thereafter c) retractable to a proximal position whereby it disengages from the portion of the elongate flexible catheter and allows both the proximal and distal expandable areas to assume non-elongated radially expanded configurations;
   advancing the catheter over a guidewire which extends through the guidewire lumen of the elongate member, while maintaining the elongate member in the distal position to maintain the proximal and distal expandable areas in their elongated radially collapsed configurations;
   B) with the elongate member advanced to a position where it causes both the proximal and distal expandable areas to be in their elongated and radially collapsed configurations, advancing the catheter over the guidewire which extends through the guidewire lumen of the elongate member to a position where the proximal expandable area is in the lumen of the common blood vessel and the distal expandable area is in the lumen of the first branch blood vessel, with the second branch blood vessel emanating from a location between the proximal and distal expandable areas;
   C) retracting the elongate member to the proximal position a position whereby it allows both the proximal and distal expandable areas to assume non-elongated radially expanded configurations such that the proximal expandable area contacts the common blood vessel wall and the distal expandable area contacts the first branch blood vessel wall;
   D) advancing a treatment device through the elongate member receiving lumen, out of the treatment device outlet opening and into the lumen of the second branch blood vessel; and
   E) using the treatment device to perform or facilitate performance of a treatment of a defect in the second branch blood vessel.

2. A method according to claim 1 wherein the treatment device comprises a guidewire that is used to facilitate advancement of another treatment apparatus into the lumen of the second branch blood vessel for treatment of the defect.

3. A method according to claim 1 wherein blood flow through the common blood vessel is normally in an antegrade direction that runs from the proximal expandable region toward the distal expandable region and wherein the proximal expandable region is constructed to occlude blood flow in the antegrade direction, thereby resulting in retrograde backflow of blood in the common blood vessel and second branch vessel toward the proximal expandable area.

4. A method according to claim 3 wherein an opening is formed in the catheter such that the retrograde backflow of blood and any matter contained therein will enter the opening in the catheter and may be aspirated through that opening into a lumen of the catheter.

5. A method according to claim 4 further comprising the step of aspirating blood and any matter contained therein through the opening and into the elongate member receiving lumen of the catheter.

6. A method according to claim 4 wherein at least a distal aspect of the proximal expandable area is blood-permeable and said opening in the catheter is formed within the proximal expandable area so that blood may flow in the retrograde direction through the distal aspect of the proximal expandable area and into the opening in the catheter.

7. A method according to claim 4 further comprising the step of delivering radiographic contrast media into the blood vessels and obtaining an image of the blood vessels.

8. A method according to claim 1 wherein: the treatment device outlet opening is located within the proximal expandable area; the proximal expandable area, when in its expanded configuration, has at least one opening though which the treatment device is passable; and Step D comprises advancing the treatment device through the elongate member receiving lumen, out of the treatment device outlet opening, through an opening in the proximal expandable area and into the lumen of the second branch blood vessel.

9. A method according to claim 1 wherein at least a distal portion of the proximal expandable area is formed of a mesh which, when the proximal expandable area is in its expanded configuration, has a plurality of openings therein and wherein the treatment device is advanced through an opening in that mesh.

10. A method according to claim 1 wherein the common blood vessel is the Common Carotid Artery, the first branch blood vessel is the External Carotid Artery and the second branch blood vessel is the Internal Carotid Artery.

\* \* \* \* \*